United States Patent [19]
Gong et al.

[11] Patent Number: 5,935,783
[45] Date of Patent: Aug. 10, 1999

[54] GENES MAPPING IN THE DIGEORGE AND VELOCARDIOFACIAL SYNDROME MINIMAL CRITICAL REGION

[75] Inventors: Weilong Gong, Philadelphia; Beverly S. Emanuel, Broomall; Marcia L. Budarf, Moylan, all of Pa.; Bruce Roe, Norman, Okla.

[73] Assignees: Children's Hospital of Philadelphia, Philadelphia, Pa.; University of Oklahoma, Norman, Okla.

[21] Appl. No.: 08/775,009

[22] Filed: Dec. 27, 1996

Related U.S. Application Data

[63] Continuation-in-part of application No. 08/717,400, Sep. 20, 1996, abandoned.

[60] Provisional application No. 60/004,033, Sep. 20, 1995.

[51] Int. Cl.$^6$ .......................... C07H 21/04; C12N 15/12; C12P 19/34; C12Q 1/68
[52] U.S. Cl. .......................... 435/6; 435/91.2; 536/23.5; 536/24.31
[58] Field of Search .................................. 536/23.1, 24.3, 536/24.31, 24.33; 435/6, 91.1, 91.2

[56] References Cited

U.S. PATENT DOCUMENTS 5,576,178  11/1996  Emanuel et al. ............................. 435/6

OTHER PUBLICATIONS

Augusseau, S. et al., "DiGeorge syndrome and 22q11 rearrangements", *Hum. Genet.*, 1986, 74, 206.

Budarf, M.L. et al., "Cloning a balanced translocation associated with DiGeorge syndrome and identification of a disrupted candidate gene", *Nature Genet.*, 1995, 10, 269–288.

Carey, A.H. et al., "Molecular genetic study of the frequency of monosome 22q11 in DiGeorge syndrome", *Am. J. Hum. Genet.*, 1992, 51, 964–970.

Church, D.M. et al., "Isolatioon of genes from complex sources of mammalian genomic DNA using exon amplification", *Nature Genetics*, 1994, 6, 98–105.

Demczuk, S. et al., "Cloning of a balanced translocation breakpoint in the DiGeorge syndrome critical region and isolation of a novel potential adhesion receptor gene in its vicinity", *Hum. Mole. Genet.*, 1995, 4(4), 551–558.

Driscoll, D.A. et al., "A genetic etiology for DiGeorge syndrome: consistent deletions and microdeletions of 22q11", *Am. J. Hum. Genet.*, 1992, 50, 924–933.

Driscoll, D.A. et al., "Deletions and microdeletions of 22q11.2 in velo–cardio–facial syndrome", *Am J. Med. Genet.*, 1992, 44, 261–268.

Driscoll, D.A. et al., "Prevalence of 22q11 microdeletions in DiGeorge and velo–cardio–facial syndromes: implications for genetic counseling and prenatal diagnosis", *J. Med. Genet.*, 1993, 30, 813–817.

Duyk, G.M. et al., "Exon trapping: A genetic screen to identify candidate transcribed sequences in cloned mammalian genomic DNA", *Proc. Natl. Acad. Sci. USA*, 1990, 87, 8995–8999.

Emanuel, B.S. et al., "Molecular and phenotypic analysis of the chromosome 22 microdeletion syndromes. In: Phenotype Mapping of Down Syndrome and Other Aneuploid Conditions", Epstein, C.J. (ed.), Wiley Liss, NY, 1993, 207–224.

Feinberg, A.P. et al., "A technique for radiolabeling DNA restriction endonuclease fragments to high specific activity", *Anal. Biochem.*, 1983, 132, 6–13.

Goldmuntz et al., "Cloning, Genomic Organization and Chromosomal Localization of Human Citrate Transport Protein to the DiGeorge/Velocardiofacil syndrome minimal Critical Region", *Genomics*, 1996, 33(2), 271–276.

Gong et al., "Towards a transcription map spanning a 250 kb area within the DiGeorge syndrome chromosome region (DGCR) in 22q11", *Am. J. Human Genetics*, 1994, 55(3), p. A259, abstract 1513.

Greenberg, F. et al., "Cytogenetic findings in a prospective series of patients with DiGeorge anomaly", *Am. J. Hum. Genet.*, 1988, 43, 605–611.

Hamaguchi, M. et al., Establishment of a highly sensitive and specific exon–trapping system, *Proc. Natl. Acad. Sci. USA*, 1992, 89, 9779–9783.

Hanks, S.K. et al., "The protein kinase family: conserved features and deduced phylogeny of the catalytic domains", *Science*, 1988, 241, 42–51.

Heisterkamp, et al., "Localization of the Human Mitochondrial Citrate Transporter Protein Gene to Chromosome 22Q11 in the DiGeorge Syndrome Critical Region", *Genomics*, 1995, 29(2), 451–456.

Kirby, M.L. et al., "Neural crest and normal development: A new perspective ", *Anat. Rec.*, 1984, 209, 1–6.

Korn, B. et al., "A strategy for the selection of transcribed sequences in the Xq28 region", *Hum. Mol. Genet.*, 1992, 1(4), 235–242.

Kurahashi et al., "Isolation and Characterization of a Novel Gene Deleted in DiGeorge Syndrom", *Human Molecular Genetics*, 1995, 4(4), 541–49.

Lammer, E.J. et al., "The DiGeorge anomaly as a developmental field defect", *Am. J. Med. Genet.*, 1986 Supp. 2, 113–127.

(List continued on next page.)

*Primary Examiner*—George C. Elliott
*Assistant Examiner*—Robert Schwarteman
*Attorney, Agent, or Firm*—Woodcock Washburn Kurtz Mackiewicz & Norris LLP

[57] ABSTRACT

Transcription units encoded in the minimal DGS/VCFS critical region, primer pairs effective for amplifying said transcripts in a genomic DNA sample for the preparation of probes for detecting genetic deletions/mutations in the minimal DGS/VCFS critical region, and kits containing the probes are disclosed. One or more of said transcription units is implicated for the abnormalities associated with DGS/VCFS.

10 Claims, 10 Drawing Sheets

OTHER PUBLICATIONS

Lefebvre, S. et al., "Identification and Characterization of a Spinal Muscular Atrophy–Determinig Gene", *Cell,* 1995, 80, 155–165.

Li, M. et al., "Narrowing the DiGeorge region (DGCR) using DGS–VCFS associated translocation breakpoints", *Am. J. Hum. Genet.,* 1994, 55(3), (abstract) *Supp. No. 43.*

Lindsay et al., "A transcription Map in the CATCH22 Critical Region: Identification, Mapping and Ordering of Four Novel Transcripts Expressed in Heart", *Genomics,* 1996, 32(1), 104–112.

Lovett, M., "Fishing for complements: finding genes by direct selection", *Trends in Genetics,* 1994, 10(10), 352–357.

Maniatis, T. et al., Molecular Cloning, A Laboratory Manual, 2nd Ed., Cold Spring Laboratory Press, 1989.

Morgan, J. G. et al., "The selective isolation of novel cDNAs encoded by the regions surrounding the human interleukin 4 and 5 genes", *Nucl. Acids Res.,* 1992, 20(19), 5173–5179.

Stevens, C.A. et al., "DiGeorge anomaly and Velo–Cardio–Facial syndrome", *Pediatrics,* 1990, 85(4), 526–530.

Tagle, D.A. et al., "Magnetic bead capture of expressed sequences encoded withinlarge genomic segments", *Nature,* 1993, 361, 751–753.

Uberbacher, E.C. et al., "Locating protein–coding regions in human DNA sequences by a multiple sensor–neural network approach", *Proc. Natl. Acad. Sci. USA,* 1991, 88, 11261–11265.

Wadey, R. et al., "Isolation of a gene encoding an integral membrane protein from the vicinity of a balanced translocation breakpoint associated with DiGeorge syndrome", *Hum. Mole. Genet.,* 1995, 4(6), 1027–1033.

```
DSG-G     1 MDDATVLRKKGYIVGINLGKGSYAKVKSAYSERLKFNVAVKIIDRKKTPT  50
            ||||.||:::|||:|||||.||||||||||||||||||||||||||.|.
U01840    1 MDDAAVLKRRGYIMGINLGEGSYAKVKSAYSERLKFNVAVKIIDRKKAPS  50

DSG-G    51 DFVERFLPREMDILATVNHGSIIKTYEIFETSDGRIYIIMELGVQGDLLE 100
            ||:|:|||||::|||  :||  ||:|||||||.||||::||||||||||
U01840   51 DFLEKFLPREIEILAMLNHRSIVKTYEIFATSDGKVYIVMELGVQGDLLE 100

DSG-G   101 FIKCQGALHEDVARKMFRQLSSAVKYCHDLDIVHRDLKCENLLLDKDFNI 150
            |||..|||:||  |||.|:|||||:|||||||:||||||:|||||||||
U01840  101 FIKTRGALQEDDARKKFHQLSSAIKYCHDLDVVHRDLKSENLLLDKDFNI 150

DSG-G   151 KLSDFGFSKRCLRDSNGRIILSKTFCGSAAYAAPEVLQSIPYQPKVYDIW 200
            ||||||||||||||..||:|||||||||||||||||||:|||||||||||
U01840  151 KLSDFGFSKRCLRDDSGRLILSKTFCGSAAYAAPEVLQGIPYQPKVYDIW 200

DSG-G   201 SLGVILYIMVCGSMPYDDSDIRKMLRIQKEHRVDFPRSKNLTCECKDLIY 250
            ||||||||||||||||||:|:| |||||||:|||||:||.||||||||
U01840  201 SLGVILYIMVCGSMPYDDSNIKK.LRIQKEHRVNFPRSKHLTGECKDLIY 249

DSG-G   251 RMLQPDVSQRLHIDEILSHSWLQ 273    SEQ ID NO: 30
            |||||||..|||||||||.|:|:|
U01840  250 RMLQPDVNRRLHIDEILNHCWVQ 272    SEQ ID NO: 31
```

FIG. 3A

```
CTP      1 MPAPRAPRALAAAAPASGKAKLTHPEKAILAGGLAGGIEICITFPTEYVK  50
           |:||||||||.||||:|||||||||:||||||||||||||||||||||||
p32089   1 MAAPRAPRALTAAAPGSGKAKLTHPGKAILAGGLAGGIEICITFPTEYVK  50

CTP     51 TQLQLDERSHPPRYRGIGDCVRQTVRSHGVLGLYRGLSSLLYGSIPKAAV 100
           ||||||||.:|||||||||||||||||||||||||||||||||||||||
p32089  51 TQLQLDERANPPRYRGIGDCVRQTVRSHGVLGLYRGLSSLLYGSIPKAAV 100

CTP    101 RFGMFEFLSNHMRDAQGRLDSTRGLLCGLGAGVAEAVVVVCPMETIKVKF 150
           |||||||||||||||||||||| ||||||||||||||||||||||:||||
p32089 101 RFGMFEFLSNHMRDAQGRLDSRRGLLCGLGAGVAEAVVVVCPMETVKVKF 150

CTP    151 IHDQTSPNPKYRGFFHGVREIVREQGLKGTYQGLTATVLKQGSNQAIRFF 200
           ||||||.||||||||||||||||||||||||||||||||||||||||||
p32089 151 IHDQTSSNPKYRGFFHGVREIVREQGLKGTYQGLTATVLKQGSNQAIRFF 200

CTP    201 VMTSLRNWYRGDNPNKPMNPLITGVFGAIAGAASVFGNTPLDVIKTRMQG 250
           ||||||||.|||||||||||||||||||:||||||||||||||||||||
p32089 201 VMTSLRNWYQGDNPNKPMNPLITGVFGAVAGAASVFGNTPLDVIKTRMQG 250

CTP    251 LEAHKYRNTWDCGLQILKKEGLKAFYKGTFPRLGRVCLDVAIVFVIYDEV 300
           ||||||||:|||:||||.|| ||||||||||||||||||||||||||||
p32089 251 LEAHKYRNTLDCGVQILKNEGPKAFYKGTVPRLGRVCLDVAIVFVIYDEV 300

CTP    301 YKLLNKVWKTD 311    SEQ ID NO: 32
           |||||||||||
p32089 301 VKLLNKVWKTD 311    SEQ ID NO: 33
```

FIG. 3B

```
CLTCL      1 EAKLTDQLPLIIVCDRFGFVHDLVLYLYRNNLQRYIEIYVQKVNPSRTPA  50
             |||||||||||||||||:|||||||||||||||:|||||||||||||||.
U31357   765 EAKLTDQLPLIIVCDRFDFVHDLVLYLYRNNLQKYIEIYVQKVNPSRLPV 814

CLTCL     51 VIGGLLDVDCSEEVIKHLIMAVRGQFSTDELVAEVEKRNRLKLLLPWLES 100
             |||||||||||:|||:||:.|||||||||||||||||||||||||||||.
U31357   815 VIGGLLDVDCSEDVIKNLILVVRGQFSTDELVAEVEKRNRLKLLLPWLEA 864

CLTCL    101 QIQEGCEEPATHNALAKIYIDSNNSPECFLRENAYYDSSVVGRYCEKRDP 150
             .|:|||||||||||||||||||||.|| |||||:|||.|||:|||||||
U31357   865 RIHEGCEEPATHNALAKIYIDSNNNPERFLRENPYYDSRVVGKYCEKRDP 914

CLTCL    151 HLACVAYERGQCDLELIKVCNENSLFKSEARYLVCRKDPELWAHVLEETN 200
             |||||||||||||||||.|||||||||| .||| |||||||: || |.|
U31357   915 HLACVAYERGQCDLELINVCNENSLFKSLSRYLVRRKDPELWGSVLLESN 964

CLTCL    201 PSRRQLIDQVVQTALSETRDPEEISVTVKAFMTADLPNELIELLEKIVLD 250
             | ||.|||||||||||||.||||:|||||||||||||||||||||||||
U31357   965 PYRRPLIDQVVQTALSETQDPEEVSVTVKAFMTADLPNELIELLEKIVLD 1014

CLTCL    251 NSVFSEHRNLQNLLILTAIKADRTRVMEYISRLDNYDALDIASIAVSSAL 300
             ||||||||||||||||||||||||||||||.||||||| |||.||:..|
U31357  1015 NSVFSEHRNLQNLLILTAIKADRTRVMEYINRLDNYDAPDIANIAISNEL 1064

CLTCL    301 YEEAFTVFHKFDMNASAIQVLIEHIGNLDRAYEFAERCNEPAVWSQLAQA 350
             :||||.:|:|||:|.||:|||||||||||||||||||||||||||||.|
U31357  1065 FEEAFAIFRKFDVNTSAVQVLIEHIGNLDRAYEFAERCNEPAVWSQLAKA 1114

CLTCL    351 QLQKDLVKEAINSYIRGDDPSSYLEVVQSASRSNNWEDLVKFLQMARKKG 400
             ||||::|||:|||::|||||||:||||.|. |.|||:|||:|||||||:
U31357  1115 QLQKGMVKEAIDSYIKADDPSSYMEVVQAANTSGNWEELVKYLQMARKKA 1164

CLTCL    401 RESYIETELIFALAKTSRVSELEDFINGPNNAHIQQVGDRCYEEGMYEAA 450
             ||||:|||||||||||.|:.|||:|||||||||||||||||:||:||||
U31357  1165 RESYVETELIFALAKTNRLAELEEFINGPNNAHIQQVGDRCYDEKMYDAA 1214
```

FIG. 3C

```
CLTCL    451 KLLYSNVSNFARLASTLVHLGEYQAAVDNSRKASSTRTWKEVCFACMDGQ 500
             ||||.||||:|||||||||||||||||..|||.|||||||||||:||.
U31357  1215 KLLYNNVSNFGRLASTLVHLGEYQAAVDGARKANSTRTWKEVCFACVDGK 1264

CLTCL    501 EFRFAQLCGLHIVIHADELEELMCYYQDRGYFEELILLLEAALGLERAHM 550
             |||:||:|||||||:|||||||||||: ||||||||||| :||||||||||
U31357  1265 EFRLAQMCGLHIVVHADELEELINYYQDRGYFEELITMLEAALGLERAHM 1314

CLTCL    551 GMFTELAILYSKFKPQKMLEHLELFWSRVNIPKVLRAAEQAHLWAELVFL 600
             |||||||||||||||| |||||||||||||||||||||||||||||||||
U31357  1315 GMFTELAILYSKFKPQKMREHLELFWSRVNIPKVLRAAEQAHLWAELVFL 1364

CLTCL    601 YDKYEEYDNAVLTMMSHPTEAWKEGQFKDIITKVANVELCYRALQFYLDY 650
             ||||||||||::|||.|||:||||||||||||||||||||:|||:||||::
U31357  1365 YDKYEEYDNAIITMMNHPTDAWKEGQFKDIITKVANVELYYRAIQFYDEF 1414

CLTCL    651 KPLLINDLLLYLSPRLDHTWTVSFFSKAGQLPLVKPYLRSVQSHNNKSVN 700
             ||||:||||:|||||||||:..|..:|||. |||||||||||.|||||||
U31357  1415 KPLLLNDLLMVLSPRLDHTRAVNYFSKVKQLPLVKPYLRSVQNHNNKSVN 1464

CLTCL    701 EALNHLLTEEEDYQGLRASIDAYDNFDNISLAQQLEKHQLMEFRCIAAYL 750
             |.||:|:...||||||:||.|||||||||||||||.||||:|:|||  |||||
U31357  1465 ESLNNLFITEEDYQALRTSIDAYDNFDNISLAQRLEKHELIEFRRIAAYL 1514

CLTCL    751 YKGNNWWAQSVELCKKDHLYKDAMQHAAESRDAELAQKLLQWFLEEGKRE 800
             :|||||:| ||||||||| |||||||.|.||:|.|||:.|||||||:|:|||
U31357  1515 FKGNNRWKQSVELCKKDSLYKDAMQYASESKDTELAEELLQWFLQEEKRE 1564

CLTCL    801 CFAACLFTCYDLLRPDMVLELAWRHNLVDLAMPYFIQVMREYLSKVDKLD 850
             ||:||||||||||:||| |||||::|:|||||||||||||||:|||.||||||
U31357  1565 CFGACLFTCYDLLRPDVVLETAWRHNIMDFAMPYFIQVMKEYLTKVDKLD 1614

CLTCL    851 ALESLRKQEEHVTEPAPLVFD 871    SEQ ID NO: 34
             | ||||||:||:.||..|:|::
U31357  1615 ASESLRKEEEQATETQPIVYG 1433   SEQ ID NO: 35
```

FIG. 3C (cont.)

```
   1 cccgcgcgcggaggcagggccgccgcagtcgaggattagcgcgttcgcggccggcgctgc
  61 gggattaacccgcgtggactggacgcccggcccggggattactgcgcgctccctccccga
                                                    M  A  A  A  G
 121 cgtatatattcccgcggcggcggcgccccggccgggccgggcATGGCGGCAGCGGCTGGG
      G  A  A  S  R  R  G  A  G  R  P  C  P  F  S  I  E  H  I  L
 181 GGCGCGGCGAGCCGCCGGGGTGCCGGGCGGCCCTGCCCCTTCTCCATCGAGCACATCCTC
      S  S  L  P  E  R  S  L  P  A  R  A  A  C  P  P  Q  P  A  G
 241 TCCAGCCTGCCCGAGCGGAGCCTCCCGGCCCGGGCCGCCTGCCCACCGCAGCCCGCCGGT
      R  Q  S  P  A  K  P  E  E  P  G  A  P  E  A  A  P  C  A  C
 301 CGCCAGAGCCCCGCGAAGCCAGAGGAGCCCGGGGCGCCCGAGGCTGCGCCCTGCGCCTGC
      C  C  C  G  P  R  A  A  P  C  G  P  P  E  A  A  A  G  L
 361 TGCTGCTGCTGCGGCCCCCGCGCGGCGCCCTGCGGGCCCCCAGAGGCGGCCGCCGGGCTG
      G
 421 Ggtgagtgggcgcggagcggggcgcggggcccggcggagcccggggcgcggcgcagtggg
                                                          A  R  L
 481 tgccgagcttggccccagccccgcgcctcaccgcgccctcgctccgcagGCGCTCGTCTG
      A  W  P  L  R  L  G  P  A  V  P  L  S  L  G  A  P  A  G  G
 541 GCGTGGCCGCTGAGGCTGGGACCGGCGGTGCCCTTGTCTCTGGGTGCGCCAGCCGGAGGT
      S  G  A  L  P  G  A  V  G  P  G  S  Q  R  R  T  R  R  H  R
 601 TCCGGGGCGCTCCCGGGCGCGGTCGGCCCGGGTTCGCAGCGGCGCACGAGGCGCCACCGC
      T  I  F  S  E  E  Q  L  Q  A  L  E  A  L  F  V  Q  N  Q  Y
 661 ACCATCTTCAGCGAAGAGCAGCTGCAGGCGCTCGAGGCGCTTTTCGTGCAGAACCAGTAT
      P  D  V  S  T  R  E  R  L  A  G  R  I  R  L  R  E  E  R  V
 721 CCTGACGTGAGTACGCGCGAGCGCCTGGCCGGCCGCATCCGCCTTCGCGAGGAGCGCGTG
      E
 781 GAGGtgagtgccccgcccagcctttccccggagcgcgcgggccgcggctacactggactg
 841 gggtcctggcgggcgggcgcccttTGCAAAGACGGCCTCGGCCCAAGCCCCGCCCTGGCG
 901 cgccggagggaggaggtccctggacggcgctgggcgtccggggGTATGAGGAGCGGGTGA
 961 gagcagggaggtgccgcgggaaaggaaccggagggctacttttcttttcttttgttttac
1021 actttcctctggtgacgaaagaggcccgcgttcacgtccagaatttgggaaattcagaag
1081 agcccgcaacccaagaaggggcgtcctggtcgccgccagctggaggctggggcgggtact
1141 aaggggggttcccatctcgcgtccagacccaccgagtctgtccgcagcgaataagggcagg
1201 tggcgcgcagccgcggcccgggtgtcggctctacagcgccgtccgcccacatccctgttg
1261 cgaagctcccctctcggtccctgtgggaccctcgggagccggtgggacgcaggacctggg
                                        V  W  F  K  N  R  R  A  K  W
1321 gctagggctgagcattcccccatccccagGTCTGGTTCAAGAACCGCCGGGCCAAATGG
      R  H  Q  K  R  A  S  A  S  A  R  L  L  P  G  V  K  K  S  P
1381 CGACACCAGAAGCGCGCGTCGGCTTCCGCGAGGCTCCTGCCCGGCGTCAAGAAGTCCCCG
      K  G  S  C          SEQ ID NO: 37
1441 AAGGGGAGCTGCTGATGActctaggagctgcccctgggctcggccacccttttgggatc
```

FIG. 4A

```
1501 tttggagttggcgctgagagaagacaggtctacccgaaaaggagctgggagagtacaccg
1561 gccgcctccacccgtctccacagcccttgcctcctgcagctcgtgctgccgtggcgctgg
1621 ggacgggcccccggtgcttggtgttccacggcagtgggagtggcgagtcccttgggggtg
1681 ggctggggcatagagcagtttcctcagctccctaccccccgagagacactaactccaccg
1741 caggaggggaaccaccccgtatcaacacgggacccagaatcctacgcagtggagcgtctc
1801 tccgcaccctgggacatgctggccaccctcttctcaatgtggacattgacctaacttgac
1861 ctggctcgtcctcccccagcgggagaggggatggggttcgtgtctgtgcagtcctggcgt
1921 tgcaggcttcccaggccctgggctgggtcttggtatctggacctgtagaataagaaggtc
1981 gcaggagcgattccaggagcccctccacagtcccttccacttcgagcctcgcgctgatac
2041 tgagaaactagcaacttcaaataccacagaagccgcccagagtctcaagtccaccttggc
2101 tccactcccacacccaacaaggagctgtcccttcttcttccttcccagcgaggggggtatt
2161 tagggtacagctgtctttgagaggagcacagctcagcgatcctcagtctctgcaccaggg
2221 tgctccccagcagaggggactgctccacggatggtggccttggacccctggggtccagcc
2281 ctggcctctaggctactgtgaacctgcccatgggtgagggtcccctgcttcctcctgggg
2341 ttttcatgctgtgggctcggactccctcacagcaatctgtgccatcctagggtagggcaa
2401 gaggaggttggactggggagaccccgcccctgctgcctgggaagatgcctgccctcccct
2461 tctttatcctggcccatggcaaaaggcacagtggaaagaagccttagattccccaagtag
2521 gccctacagtgggtccaaagcatctcacatccccaccccagctggcttgagcacctcgt
2581 tctgtctccttacaggccctgcagggaatggggccattctacctgcaagagatgaagtcc
2641 atctctaaaagcaggactgcagaagccagggctgcagctccccagacaccccaaggctgg
2701 ccagcttggataacaccaagcaagcatggtgtccccagtcagaactgccctgacactgct
2761 gggtgtccctagcatccccgcctccacccctagcatgcacacaaagcccttctccctgaa
2821 ccctggtcttgcccttggggactgaacagactacctgtggacatgcccgtgtcccagtca
2881 gctcccttgcagctggggacactcgcatctcacaggctccaggccccttgagttccttgg
2941 ttgaatggccatctgtcattgttttgggagccccgatcagagcttgtggagcgccacctt
3001 ccagggctcagtggctgtgttgctctcctgaatttgcttcttgagctctagctgctcctt
3061 ggcaggctgaccccccacagcaggctattaacataggcatccttcacgctcacacccagg
3121 cgctcgcttctcatcttcaccctcttcccggtttatcttttaccctcagactccaattcc
3181 catctttctgccacatttacatctcaagccaggcacttcccctgagccaggtatttatct
3241 ccagctgtccccttgaagcccacagactccttaaggtcaccttgtccacagtgagctctt
3301 ctgtgcaaaccaggcacatgagccagagagctagccgcccacccgaaactggtccctgga
3361 cccctccctctcctgatcatccactatacccaggctgacaggaagtcagttttactgttt
3421 atcaataaatcaataaatcccagaatctctccagctctaactgcaccagtctgatgtaag
3481 ccaccgtcacctctcaccttgaccact    SEQ ID NO: 36
```

FIG. 4A (cont.)

```
GSC    kRRHRTIFtd  EQLeALEnLF  qetkYPDVgT  REqLArkvhL
GSCL   tRRHRTIFse  EQLqALEaLF  vqnqYPDVsT  RErLAgrirL
                    ▽        *
GSC    REEkVEVWFK  NRRAKWRrQK        SEQ ID NO: 38
GSCL   REErVEVWFK  NRRAKWRhQK        SEQ ID NO: 39
```

GENES MAPPING IN THE DIGEORGE AND VELOCARDIOFACIAL SYNDROME MINIMAL CRITICAL REGION

This application is a continuation-in-part of U.S. application Ser. No. 08/717,400, filed Sep. 20, 1996, abandoned, hereby incorporated by reference in its entirety, which claims the benefit of provisional application 60/004,033 filed Sep 20, 1995.

The Government may have rights in this invention.

TECHNICAL FIELD

The present invention relates to the identification of transcription units in the minimal DiGeorge critical region, as well as primers and probes thereto.

BACKGROUND OF THE INVENTION

DiGeorge syndrome (DGS) is a developmental anomaly of the derivatives of the 3rd and 4th pharyngeal pouches. It results in a variety of malformations including absence of hypoplasia of thymus and parathyroids, cardiovascular anomalies and mild craniofacial dysmorphia.

It has been proposed that the primary defect in DGS is due to the failure of cephalic neural crest cells to migrate properly during early embryonic development (Kirby et al., 1984; Lammer and Opitz). Previously, cytogenetic studies of patients with DGS demonstrated that ~20% had chromosomal abnormalities, with the majority of these chromosomal rearrangements involving the loss of the proximal long arm of chromosome 22 (rev. Greenberg, 1988). These results suggested that monosomy for 22q11 may play a significant role in the etiology of DGS. Subsequently, molecular studies have demonstrated the validity of this hypothesis (Driscoll et al., 1992a; Carey et al., 1993) and microdeletions have been detected in 89% of the patients we have studied with DGS (Driscoll et al., 1994).

Velo-cardio-facial syndrome (VCFS) is a common autosomal dominant disorder characterized by cleft palate, cardiac anomalies, typical facies and learning disabilities. Due to the phenotypic overlap between VCFS and DGS it was suggested that both diseases might share a common pathogenesis or be etiologically related (Stevens et al., 1990). Using the 22q11.2 markers found to be hemizygous in DGS, it was possible to demonstrate that VCFS patients are deleted for the same region (Driscoll et al., 1992b). Currently, over 85% of the carefully selected patients we have studied with a diagnosis of VCFS have microdeletions of 22q11.2. These findings indicate that haploinsufficiency of this region is also a major factor in the etiology of this disorder (Driscoll et al., 1994).

The region commonly deleted in the majority of DGS/VCFS patients has been estimated to be greater than 1.4 Mb, based on pulsed-field gel analysis. Further, the region deleted in individual patients can extend both proximally and distally (Drisoll et al., 1992a).

Using translocation breakpoints and fluorescence in situ hybridization analysis (FISH), the DGS/VCFS chromosomal region (DGCR) has been narrowed to 250 kb in the vicinity of D22S75 (N25) (Li et al., 1994). The only known balanced translocation associated with the DGS/VCFS phenotype, the ADU/VDU t(2:22), maps within this 250 kb region (Augusseau et al., 1986; Budarf et al., 1995). These data suggest that one or more of the genes in this minimal DGS/VCFS chromosomal region (mDGCR) are strong candidates for involvement in the pathogenesis of these disorders.

The construction of a detailed transcription map covering the complete DGCR, with emphasis on the minimal critical region, is an essential step in the identification of genes important to the etiology DGS/VCFS. In the present study, we have identified genes encoded in the mDGCR using a cDNA selection-based approach. Concurrent with the construction of this transcription map, large-scale genomic sequence of the cosmids covering the mDGCR has been performed (Roe et al., in preparation).

The availability of genomic sequence permitted the unambiguous verification of transcripts, the determination of the direction of transcription and the identification of intron-exon structure. Further, the use of GRAIL and BLAST programs assisted in the assembly of the cDNA clones into transcription units. Here we report the identification, now, of at least 12 genes in the 250 kb of the mDGCR by this combined cDNA selection and DNA sequencing approach. These genes can be considered candidates for the major features of DGS/VCFS.

SUMMARY OF THE INVENTION

In one aspect, the present invention relates to a novel transcription unit GSCL encoded in the mDGCR In another aspect, the present invention relates to the detection of genetic deletions/mutations associated with at least one condition selected from the group consisting of DiGeorge syndrome, Velocardiofacial syndrome, and cleft palate in a human patient using detectably labeled nucleic acid probes complementary to the transcription unit GSCL.

BRIEF DESCRIPTION OF THE DRAWINGS

FIGS. 3a–c: Comparison of the deduced amino acid sequences. Numbers refer to the positions in the protein sequences. Identical residues are represented by vertical lines. Similarities are indicated by one dot or two dots with two dots representing greater similarity. A. The top line represents the amino acid (aa) sequence of DGS-G and the lower line represents the amino acids sequence of the mouse serine/threonine kinase (U01840). All 14 of the most highly conserved amino acids are indicated by asterisks (*). The consensus in subdomain VI and VIII (as designated in Hanks et al., 31) are shown within frames. B. Amino acid sequence alignment of CTP (top) and the rat mitochondrial tricarboxylate transporter (P32089) (bottom). C. Comparison of amino acid sequences of CLTCL (top) and bovine clathrin heavy chain mRNA (U31357).

FIGS. 4a–b: Genomic structure and amino acid sequence of GSCL. (a) Genomic sequence of GSCL showing the amino acid translation of the predicted protein product. The amino acids corresponding to the octapeptide and to the homeodomain are shown in bold. A TATA-like element and two potential polyadenylation signals are shown in bold. The locations of primers used for PCR are underlined. The direction of transcription is from telomere to centromere. (b) Comparison of human GSC and GSCL in the homeodomain. The arrowhead denotes the conserved splice site found in all members of the goosecoid family. The lysine at position 50 (K*) is marked by an asterisk. Identities are shown as bold, upper case letters.

DETAILED DESCRIPTION

While most of the genes predicted by computational methods also were identified by experimental approaches, there was a notable exception. Data base searches using the genomic sequence of cosmid 79 h 12 identified what appeared to be a functional gene with similarity to the homeodomain family of transcription factors. This gene has highest identity to goosecoid (gsc), a gene that is expressed in neural crest-derived tissues (Gaunt et al. 1993) and required for proper craniofacial development in mice (Yamada et al. 1995; Rivera-Perez et al. 1995). The genomic structure of this gene, goosecoid-like (GSCL), is disclosed herein, as are reverse transcriptase-polymerase chain reaction experiments depicting that it is expressed during early fetal development. This early expression, together with the known role of homeobox-containing proteins in embryogenesis, make GSCL an outstanding candidate for some of the developmental abnormalities seen in DGS/VCFS.

Figure 6:
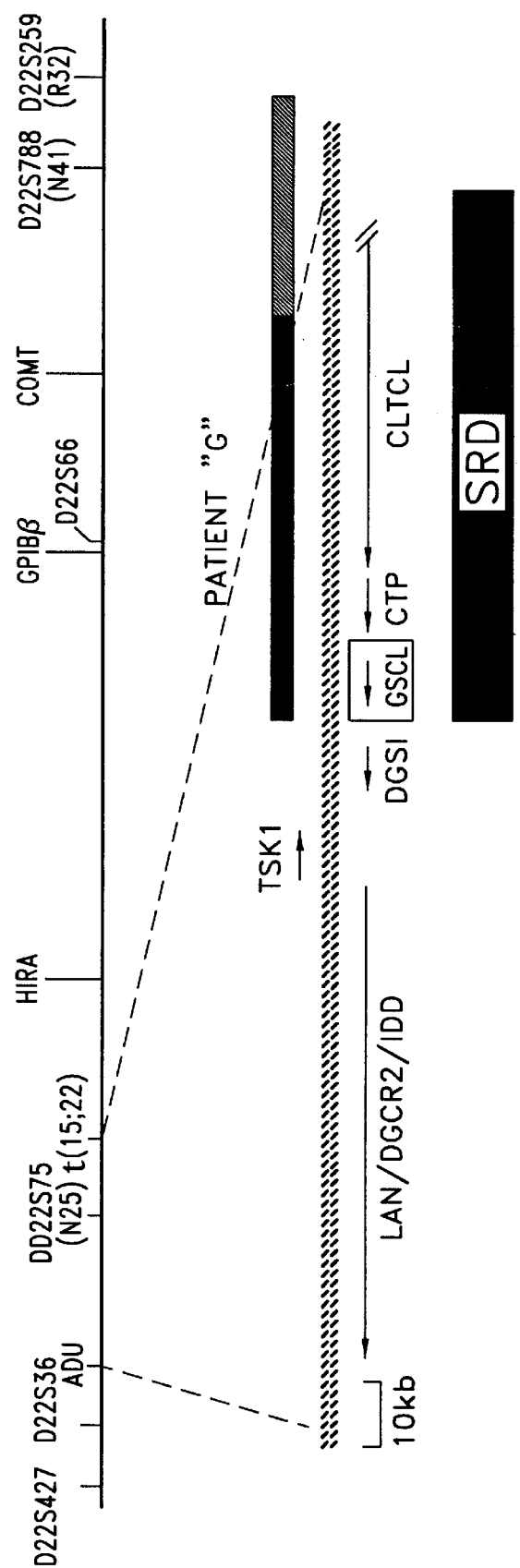
FIG. 6: Diagram of the DiGeorge chromosomal region depicting GSCL. The top part of the figure corresponds to the region on chromosome 22 that is commonly deleted in DGS/VCFS patients. The expanded region corresponds to the minimal DiGeorge critical region (mDGCR). The positions and directions of transcription of genes in the mDGCR are indicated by arrows. SRD=smallest region of deletion.

Including GSCL, we have now characterized the complete open reading frame of at least six genes in the minimal critical region (this report; Goldmuntz et al. 1996; Gong et al. 1996; Holmes et al. 1996). These genes and their directions of transcription are shown on the bottom lines in FIG. 6. Approximately 90% of all patients diagnosed with DGS/VCFS have large deletions of chromosomal region 22q11.2 that delete all of these genes (Carey et al. 1992; Driscoll et al. 1993). Although the size of the deletion is generally large, 1–2 Mb, it has been possible to define a smallest region of deletion overlap by mapping, the deletion endpoints and positions of translocation breakpoints in a series of DGS and VCFS patients (FIG. 6). In all but one case (Kurahashi et al. 1996), the deletions analyzed result in haploinsufficiency of GSCL, including a recently-described DGS patient who has an atypical proximal deletion boundary (Patient "G"; Levy et al. 1995).

The centromeric deletion boundary of the interstitial deletion in Patient "G" recently has been positioned immediately distal to DGSI (FIG. 6) (Rizzu et al. 1996). Therefore, Patient "G" narrows the centromeric boundary of the mDGCR and appears to exclude the breakpoint region of the only known balanced translocation in a patient with DGS (ADU; Augusseau et al. 1986). Perhaps the ADU translocation effects expression of downstream genes through a position effect. Our distal deletion boundary is defined by an unbalanced 15;22 translocation in a patient with classic features of VCFS (Jaquez et al. in press; Driscoll, unpublished data). If the breakpoints of these two patients ("G" and t(15;22)) can be combined to define the "smallest region of deletion" (SRD) for DGS/VCFS, then LAN/DGCR2/IDD, TSKI, and DGSI are less likely to be candidate genes. Only CLTCL, GSCL and CTP reside within the SRD.

CLTCL is unlikely to be responsible for the major defects seen in DGS/VCFS since a patient with a balanced translocation that disrupts this gene exhibits some of the features of VCFS, such as facial dysmorphia and the characteristic non-verbal learning disorder (Moss et al. 1995), but does not have other common features of the syndrome such as a heart defect or immune deficiency (Holmes et al. 1996). The other gene, CTP or citrate transport protein, a mitochondrial inner membrane protein, remains a candidate gene based on its genomic location. However, it is important to note that mutations in enzymes such as CTP tend to cause autosomal recessive disorders, whereas the 22q deletion syndrome is an autosomal dominant condition. In contrast, several diseases in humans are known to be caused by a mutation in a single copy of a homeobox-containing gene (see Noll 1993 for review; Brunelli et al. 1996). This observation, together with the potential role of GSCL as a developmental control gene, make GSCL a more likely candidate for playing a causative role in this disorder.

Proof that GSCL is responsible for some or all of the features of DGS/VCFS will rely ultimately on finding patients with the disorder who have mutations or small deletions within the gene. Among the small group of non-deleted patients we have analyzed, we have not yet detected such mutations in GSCL. These results may not be surprising since the etiology of DGS/VCFS is heterogeneous, including exposure to teratogens, maternal diabetes and other chromosomal loci (Lammer and Opitz 1986). Furthermore, since the patients we have studied are sporadic we do not know whether their disease phenotype is linked to chromosome 22.

Similarity comparisons indicate that GSCL is the closest known homolog, of gsc. Expression studies of gsc in mouse embryos demonstrate an early, transient phase of expression in the primitive streak (6.4 to 6.8 d) (Blum et al. 1992) and a later phase, beginning at 10.5 days in the craniofacial region, in derivatives of cephalic neural crest cells (Gaunt et al. 1993). The gsc-null knockout mouse has numerous craniofacial defects (Yamada et al. 1995; Rivera-Perez et al. 1995) primarily in structures derived from the first and second pharyngeal arches, the regions corresponding to highest gsc expression (Gaunt et al. 1993). While the craniofacial abnormalities observed in DGS/VCFS may be due to defects in the first and second arches, the thymus, the parathyroid glands and the conotruncal region of the heart, are derived from the third and fourth pharyngeal pouches and arches. Therefore, an attractive hypothesis is that GSCL is expressed more posteriorly than GSC and controls the differentiation of these more posterior structures.

Interestingly, the knockout of gsc did not have an effect on gastrulation, which has led to the suggestion of the existence of a second goosecoid gene (Yamada et al. 1995; Rivera-Perez et al. 1995). We propose that GSCL could represent this second locus even though the sequence homology between GSCL and GSC is restricted primarily to the homeodomain. In support of this proposal, recent experiments have shown that D-gsc is able to rescue UV-irradiated Xenopus embryos in a manner similar to X-gsc (Goriely et al. 1996) and, as is the case for GSCL, the sequence homology of D-gsc to vertebrate gsc is primarily confined to the homeodomain.

In summary, we initially established a detailed transcriptional map covering the mDGCR which identified 11 genes. All genes isolated in this region can be candidate gene(s) for DGS/VCFS, because they are deleted in most of patients with DGS/VCFS. We have now identified GSCL, a homeobox gene that maps within the smallest region of deletion of the mDGCR. Its expression in early human development and predicted function as a DNA-binding(y protein make it an outstanding candidate for many of the developmental defects associated with these disorders.

Materials and Methods

Except as otherwise noted, the procedures were performed as follows.

cDNA selection—cDNA selection was performed using a modified protocol (B. Korn, incorporated herein by reference). cDNAs were synthesized from poly (A+) mRNA prepared from fetal brain (FB), fetal liver (FL) and adult skeletal muscle (ASM) (Clontech). Reverse transcription was performed separately for each tissue using 2.5 mg of mRNA, 150 ng of random hexamers (GIBCO BRL) and 500 units of reverse transcriptase (GIBCO BRL) in a 50 ml reaction. cDNA from each source was tagged using tissue specific (tissue-marked) linkers which were ligated to the blunt-ended cDNAs. Each ligation reaction was passed through a Chroma spin-1000 (Clontech) to remove small cDNA molecules (<429 bp) from the samples and then dissolved in 50 ml $H_2O$. Of 50 ml cDNA produced, one ml was PCR amplified using primers specific for each linker:

FB: 5' -CTCTAGAACTAGTGGATCCATACG-3'[SEQ ID NO:1];

FL: 5' -CTCTAGAACTAGTGGATCACTGG-3'[SEQ ID NO:2]; and

ASM: 5' -CTCTAGAACTAGTGGATCTACCTG-3'[SEQ ID NO:3];

in a 100 ml reaction containing 10 mM Tris-HC, pH 8.3, 2.5 mM MgCl2, 50 mM KCl, 0.25 mM each of dNTPs, 0.5 mM each primer, and 2.5 units of Taq polymerase. The PCR reaction was performed with a 5 minute denaturation step at 95° C. and then subjected to 30 cycles of denaturation (45 sec. at 95° C.), annealing (45 sec. at 65° C.), extension (3 min.) and final extension was 7 min. at 72° C. using a 9600 thermal cycler (Perkin-Elmer). Purified DNA (100 ng each) from seven cosmids covering the mDGCR were pooled and biotinylated using a nick translation kit (BRL) for subsequent steps. The human repeats present in genomic DNA were suppressed by prehybridization with human Cot-1 DNA (500 mg/ml) and total human placental DNA (500 mg/ml) for 1–3 hours, and then hybridized to the amplified cDNAs in solution. The cosmid/cDNA complexes were captured on streptavidin-coated magnetic beads (Dynal), which were pretreated with 10 mg of human Cot-1 DNA (BRL) for an hour at room temperature. The specific cDNAs were separated from the beads by heating for 10 min. at 75° C. and were PCR amplified. After a second round of selection the eluted cDNAs were PCR amplified with the primers described above with the addition of a 12-nucleotide $(CUA)_4$ sequence to the 5'-end.

The PCR products were treated with UDP glycosidase, cloned into vector pAMP 10 (BRL) and transformed into DH5a cells. Single colonies were plated on LB agar and then picked into wells of 96 well microtiter dishes. Gridded arrays on nylon membranes (Amersham) were prepared using a bio-mek 1000 robot (Beckman).

DNA preparation—DNA from cosmid and cDNA clones was prepared from 5 ml cultures in LB media containing 30 mg/ml kanamycin and 50 mg/ml ampicillin, respectively, by standard methods (Sambrook et al., 1989, incorporated herein by reference).

Southern and Northern hybridization probes including cosmid insets, cDNAs, and PCR products were labeled with a-$^{32}$P dCTP by using the random priming method (Feinberg and Vogelstein, incorporated herein by reference). Human repetitive sequences were removed by prehybridization with sheared human placental DNA (250 mg/ml) and human Cot-1 DNA (125 mg/ml). The prehybridization was carried out in 0.5M $Na_2PO_4$ pH 7.3, 7% SDS, 1 mM EDTA, pH 8, at 65° C. for 3–4 h and hybridization was performed under the same condition for 16–24 h. The filters were washed twice with 0.2×SSC and 0.1×SDS at 65° C. after Southern hybridization and twice with 0.1×SSC and 0.1×SDS after Northern hybridization at 65° C. for 15–25 min each. The filters were then exposed to Kodak X-OMAT film for several hours to several days at −70° C. with an intensifying screen.

RT-PCR cDNA was synthesized in a 50 μl reaction using 100 ng of poly(A) RNA extracted from various tissues. The RNA was heated with random and oligo(dT) primers for 5 min at 65° C. and cooled to room temperature for 10 min. Reverse transcription was performed at 37° C. for 1 h after adding 5 μl 10×RT buffer (Stratagene), 20 U Rnase inhibitor (Stratagene), 2 μl of 0.1M dNTPs and 50 U MMLV reverse transcriptase. The cDNA mixture was then heated for 5 min at 90° C. For PCR amplification, 2 μl of cDNA was used per 50 μl reaction.

STS generation

Primer pairs of PCR were generated for the cDNA contigs (FIG. 1B and Table 1). Sequence data from an ABI automated sequencer was analyzed (Staden package; 21) and STSs were chosen using PRIMER version 0.5 (M.J. Daly, S. Lincoln and E. S. Lander, Whitehead Institute, Cambridge, Mass. 1991). Using the following conditions, a unique PCR fragment was obtained for each primer pair. PCR was performed 20 μl reactions using approximately 50 ng genomic DNA or 5 ng cDNA synthesized from poly(A) RNA in 1×PCR buffer: 10 mM Tris-HCl, pH 8.3, 1.0–1.5 mM $MgCl_2$, 50 mM KCl, 1 μM primers (final concentration) and 0.5 U Taq polymerase (Perkin Elmer Cetus or Boehringer-Mannheim). PCR conditions were: a 5 min denaturation step at 95° C. followed by 30 cycles of denaturation at 95° C. for 15 s, annealing at a temperature determined for each STS for 15 s, and extension at 72° C. for 1 min 22 s, and lastly a 7 min extension at 72° C. Primer sequences are summarized in Table 1.

Consistent with GDB nomenclature, we have called these PCR products sequence tagged sites (STSs) rather than expressed sequence tags (ESTs). In general, the term EST has been used to refer to partial sequence obtained from randomly isolated cDNAs. In contrast, the cDNA sequences which were used for STS generation in this study have been precisely mapped, amplify the same size fragment in cDNA as genomic DNA, and have been completely sequenced. These STSs were used in the construction of the cDNA contigs and serve as landmarks for the transcripts.

RACE-PCR

Marathon-Ready™ human fetal and skeletal muscle cDNAs (Clontech) were used in PCR using an anchor primer provided by the manufacturer and a gene-specific primer. PCR was performed in 50 μl reactions using 1×PCR buffer (Clontech): 40 mM Tricine-KOH, 15 mM KOAc, 3.5 mM Mg(OAc)$_2$, 75 mg/ml bovine serum albumin and 0.25 U KlenTaq-1 DNA polymerase (Clontech). PCR conditions were: a 1 min denaturation step at 94° C. followed by 30 cycles of [denaturation at 94° C. for 30 s, annealing and extension at 68° C. for 3 min] and lastly a 3 min extension at 68° C. The majority of PCR reactions were performed on Perkin Elmer 9600 thermal cyclers. PCR products were analyzed by gel electrophoresis using 1.5% agarose.

DNA—sequencing Double-stranded plasmid DNA was purified using the Wizard DNA purification kit and sequenced from both ends on an ABI 370A sequencer using the universal forward and reverse M123 fluorescent primers. PCR products were purified using the same purification kit and directly sequenced using the primers specific for PCR amplification.

The sequences for the transcription units have been deposited in GenBank. All aspects of the sequence deposit are incorporated herein. The accession numbers in GenBank are as follows: DGS-A: L77571; DGS-B:L77579; DGS-C:L77560*; DGS-D:L77561*; DGS-E:L77562*; DGS-F:L77563*; DGS-G:L77564*; DGS-H:L77565*; DGS-I:L77566*; DGS-J:L77567; and DGS-K:L77568. For the accession numbers followed by a single asterisk, the corresponding genomic sequence has accession number L77570; for accession numbers with a double asterisk, the corresponding genomic sequence has accession number L77569.

cDNA selection

A cosmid contig representing a 250 kb genomic region including the 22q11.2 marker D22S75 and the balanced 2;22 translocation breakpoint (ADU/VDU) has been constructed (Budarf, et al., 1995). From this contig, seven minimally overlapping cosmids were used to select region-specific cDNAs. In order to increase the complexity of the starting material, poly(A) RNA from fetal brain, fetal liver and adult skeletal muscle was used to synthesize the cDNA. The biotinylated cosmid DNA was hybridized to the amplified cDNAs in solution, and the region-specific cDNAs were eluted, PCR amplified, subjected to a second round of selection, and cloned into the pAMP10 vector. In total, 570 colonies were selected, gridded on nylon filters, and used as a cDNA reference sublibrary. To avoid analysis of cDNAs detected by cross-hybridization to non-specific sequences, the sublibrary filters were hybridized to the Alu (Blur 8) and pAMP10 probes. Of the 570 cDNAs, 34 cDNA clones gave strong hybridizing signals to the Alu probe, suggesting that they contain homologous sequences to human highly repetitive elements. After hybridization with the pAMP10 vector, an additional 23 clones produced a strong signal after a short exposure. After PCR-amplification and restriction analysis with SpeI, these clones were found to have small or no insert and they were excluded from further analysis.

To assess the specificity of the cDNA sublibrary, several cDNA clones and RT-PCR products which we had previously mapped into the mDGCR were used as positive controls. Greater than 10% of the cDNA sublibrary (60/570 clones) were identified with these probes (Table 1), indicating that the library was greatly enriched for cDNAs originating from the mDGCR.

The next step was to regionally assign the cDNA clones by hybridizing each of the 7 cosmids to the cDNA grids. 432 cDNAs including the 60 clones detected by the control probes and 5 Alu-positive cDNAs were identified.

Further, an additional 50 cDNAs, which failed to give a positive hybridization signal using radiolabeled whole cosmid insert DNA, were subsequently detected by cDNA walking or with the use of RT-PCR products (see below). In total, 482 cDNAs from the cDNA sublibrary (85%) mapped back to the 250 kb mDGCR. Of the 482 cDNAs, 130 clones were derived from fetal brain, 122 clones from fetal liver, and 230 clones from adult skeletal muscle.

As the first step toward construction of cDNA contigs, positive cDNA clones were identified by the individual cosmid screening as described above. cDNA clones positive for two adjacent cosmids were assigned into groups and positioned on overlapping regions of adjacent cosmids.

Figure 2A:
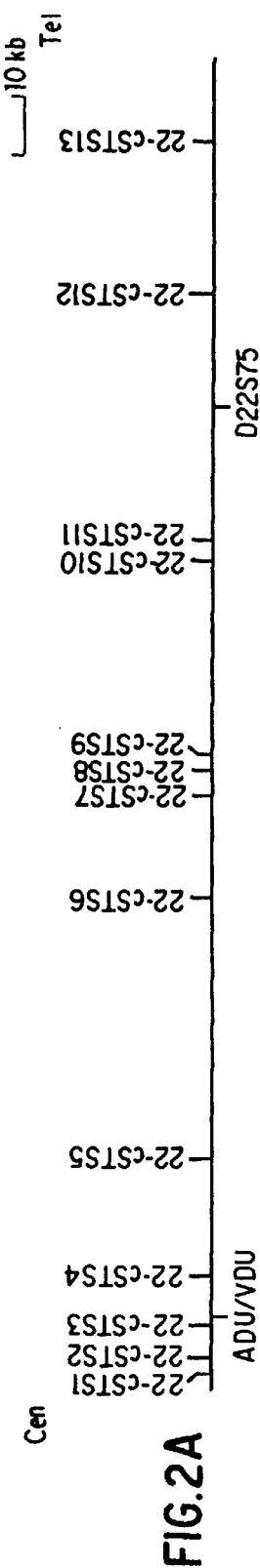
FIGS. 2a–d: Integration of cosmid map and transcription map for DGS-A through DGS-K in the 250 kb of mDGCR. A: STS markers including random marker D22S75 (N25) and gene-based STS generated by PCR with primers derived from cDNA shown in Table 3. B: Cosmid map covering the 250 kb genomic region. C: The cDNAs identified by cosmids were assembled into 16 contigs. The gaps between contig 5 and 6, and between contig 14 and 15, indicated by arrows, were joined by RT-PCR products generated using primers derived from end sequences of the corresponding contigs. Contig 6 is extended to its 5' direction by 5'RACE fragment shown in line of dashes. D: Transcription map consisting of 11 genes shown in Table 2. the orientation of transcripts are indicated by arrows. The two lines of dashes indicate two strands of DNAs. Several lines between the top and bottom lines of dashes indicate the intronless expressed sequences, whose transcriptional direction is unknown.
Figure 2B:
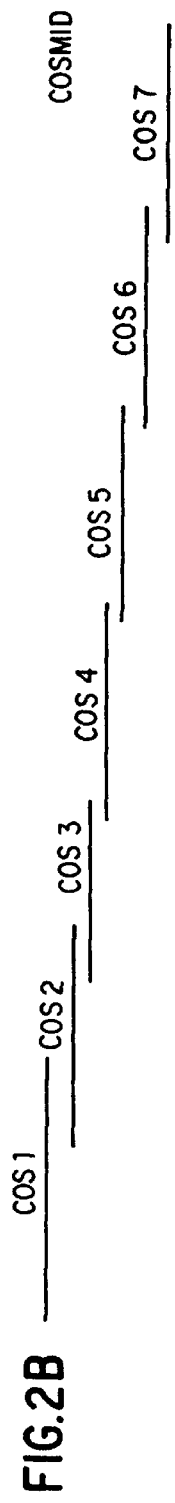
Figure 2C:
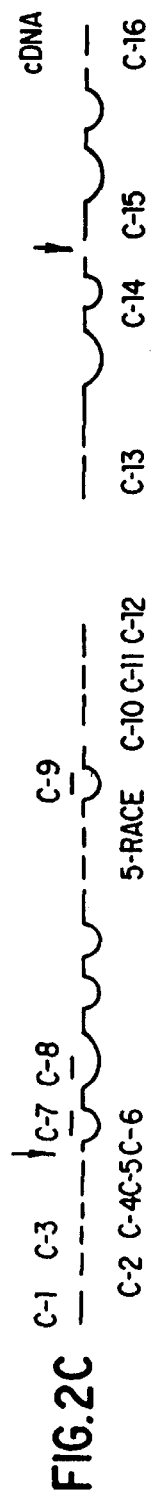

Likewise, the cDNAs recognized only by one cosmid were assembled into groups on the non-overlapping regions of cosmids. This allowed us to organize all 432 cDNA clones initially selected by the 7 cosmids into 13 groups. The cDNA clones in each group were subdivided according to the size of their inserts which was determined by CPR amplification. Further, 2–3 clones from each subgroup were chosen for cDNA walking and DNA sequencing. In total, 50 selected cDNA were fragments hybridized back to the cDNA grids to identify overlapping clones and 98 cDNA clones were completely or partially sequenced. Based on the hybridization and sequence data, 16 contigs with minimally overlapping cDNA clones were constructed (FIG. 2C and Table 2).

Figure 1:
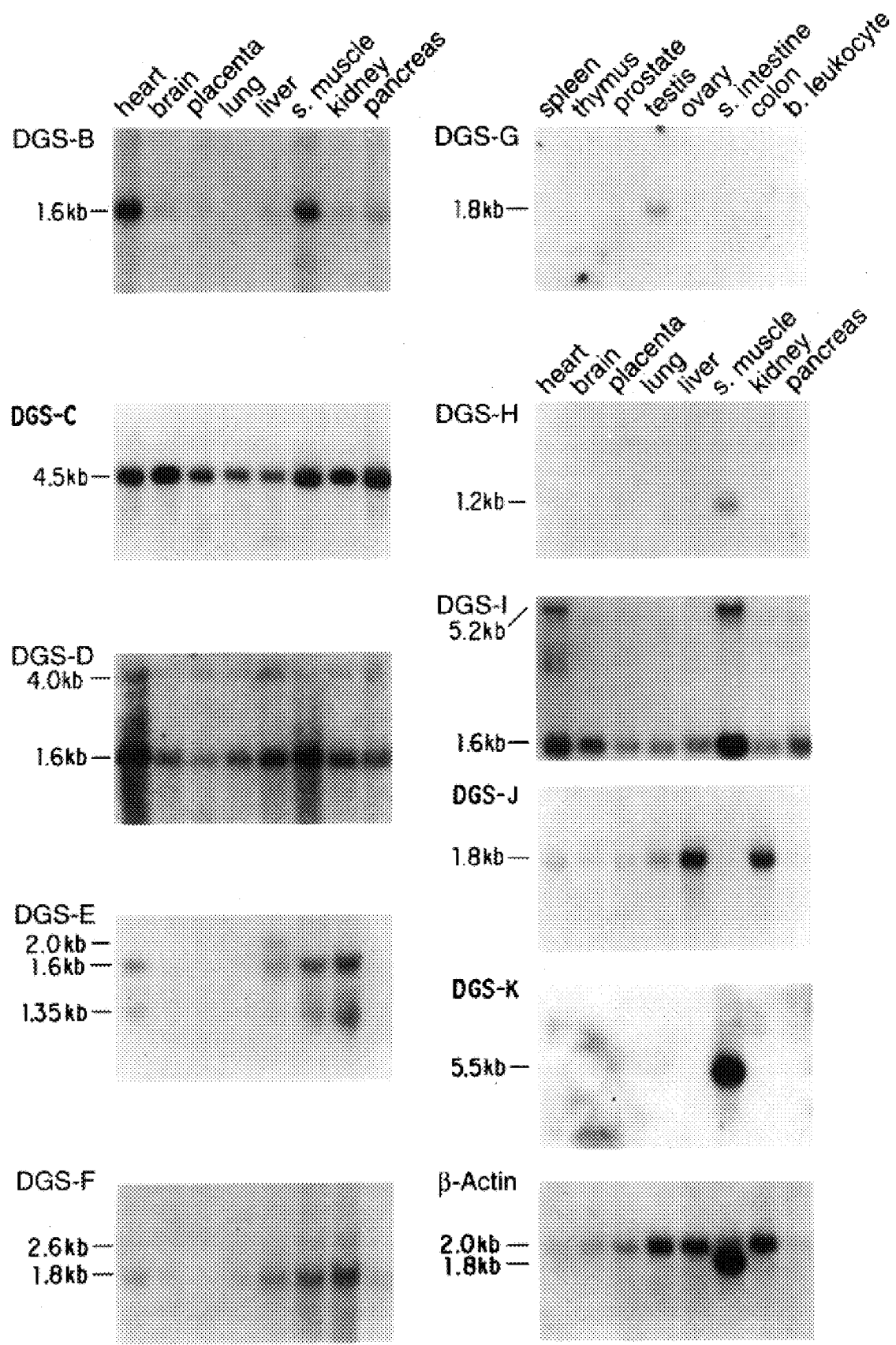
FIG. 1: Transcript units were detected by hybridization of cDNAs from DGS-B—DGS-K to multiple northern blots (Clontech).

The location of each contig was determined by hybridization of cDNAs from a given cDNA contig to Southern blots containing EcoR I- Hind III digests of cosmids representing the region (FIG. 1). Recently, 235 kb of genomic sequence of the 250 kb region has been generated (Roe et al. unpublished). Comparison between the cDNA and genomic sequence showed that 94 of 98 cDNA clones (94.8%) demonstrate 98–100% sequence identity to the corresponding cosmids, indicating the high specificity of this cDNA sublibary. Further, this combined sequence and hybridization data allowed us to precisely position the cDNA contigs on the genomic map. Only four clones, which hybridized to the cosmids, did not match the corresponding genomic sequences. Two of them are mitochondrial cDNAs, one has a high degree of identity to human skeletal a-actin, and the remaining reveals sequence similarity to human myosin heavy chain mRNA.

EXAMPLE 1

Initial Assembly of genes (transcription units)

Based on clone overlap, the smallest number of cDNA contigs that could be assembled was 16. To further assemble these contigs into genes, additional experiments were performed. The criteria for assembly of genes consisted of (i) detection of the same pattern of transcripts on Northern blot analysis (ii) identification of high similarity with the same protein or gene by sequence analysis and (iii) generation of a specific RT-PCR product using primers derived from sequences of two neighboring cDNA contigs. According to these criteria, we assembled 11 genes (DGS-A through DGS-J) in the 250 kb of the mDGCR (FIG. 2D and Table 2).

Figure 2D:
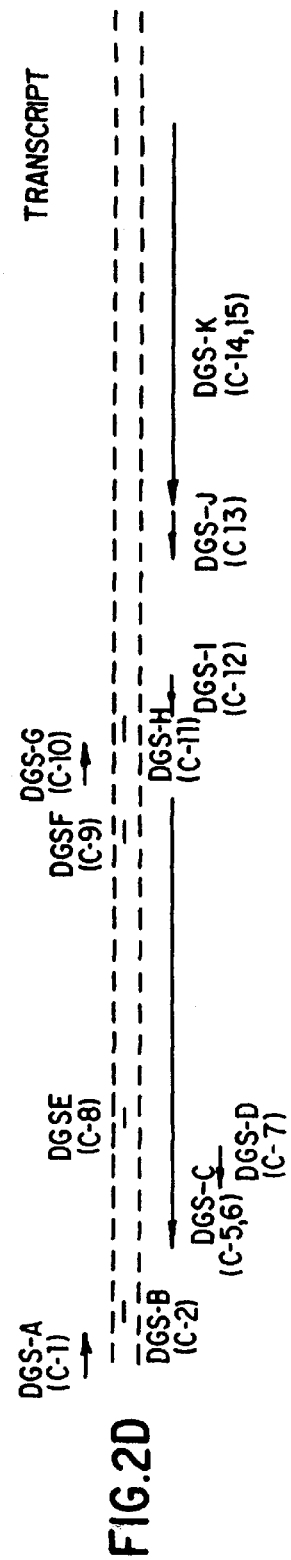

DGS-A was assembled by 11 cDNA clones from cDNA contig 1, which lies in the most centromeric region of the mDGCR (FIG. 2D). All cDNA clones in contig 1 are derived from the fetal brain mRNA. Northern hybridization with cDNAs from this contig did not give a positive signal for any of the 16 different tissues tested (see FIG. 1), but RT-PCR products of expected size were successfully amplified from fetal brain and skeletal muscle mRNA using primers derived from the contig (22-cSTS 1, Table 3). These results suggest that this is a low abundance transcript. Based on the combined sequence data, contig 1 represents 2.3 kb of expressed sequence containing no introns. The presence of a poly (A) tail in the 3' end of DGS-A indicates its orientation as being centromere to telomere (5'=C63'). Further, six ESTs (Table 2) were detected in the EST database (dbEST) with greater than 97% homology to this transcript. The dbEST ESTs were also derived from fetal brain cDNAs. Searching nucleotide and amino acid sequence homology using the BLAST email server at the National Center for Biotechnology Information (NCBI), a match was obtained with the human membrane protein-like protein (HMPL, Accession No. U21556). However, the open reading frame (ORF) of DGS-A predicted by GRAIL is in the opposite strand of the HMPL protein.

DGS-B was represented by 7 cDNAs from contig 2 and identified a 1.6 kb message in several tissues with strongest signal in heart and skeletal muscle (FIG. 1 and Table 2). This transcript has been previously described (Budarf, et al., 1995) and referred to as DGCR4. Similarity searches of nucleotide and protein databases did not demonstrate any significant matches. Primers between cDNA contig 1 and contig 2 failed to amplify a RT-PCR product, indicating that the two contigs are not derived from a single gene. This result is consistent with the Northern blot analysis of the two contigs.

Contig 3 consists of 9 cDNAs, 8 of them were derived from skeletal muscle and one from fetal brain. Using primers from the contig, a 283 bp RT-PCR product was generated from skeletal muscle and fetal brain, but not from fetal liver (22-cSTS3, Table 3). These results indicate that the transcript is not expressed in liver or is in low abundance. On northern blot analysis, the cDNAs from contig 3 did not detect any mRNAs. Comparison of the sequence of contig 3 and the corresponding cosmid showed that contig 3 is 2.2 kb centromeric to the ADU/VDU breakpoint (Budarf et al., 1995) and represents a 786 bp expressed sequence without introns. These data indicate that this contig may represent the 3' or 5' flanking sequences of a gene.

Contig 4 consists of one cDNA clone derived from fetal liver mRNA. Similarly, this cDNA failed to identify mRNAs on northern blot analysis. Sequencing of the cDNA and the corresponding genomic DNA led to the identification of two exons separated by a 120 bp intron in contig 4, which is ~5.9 kb telomeric to the ADU breakpoint. To date, we have been unable to assemble contigs 3 or 4 with the other cDNA contigs. Thus, based on the data obtained by cDNA-selection, we conservatively estimate there are at least two genes (DGS-A and -B) tightly clustered in the most centromeric 20 kb of the mDGCR.

DGS-C was assembled from cDNA contigs 5 and 6. Contig 5, consisting of 24 clones, was identified by a novel partial cDNA, LAN (Table 1). The original cDNA was isolated from a human fetal brain cDNA library probed with cosmid 1 (FIG. 2). LAN has a 2.4 kb insert and recognizes a 4.5 kb transcript expressed in all tissues tested (Budarf et al., 1995). cDNA clones from contig 6 also identified a transcript of similar size and tissue distribution to LAN, suggesting that these two contigs might be derived from the same transcript. To close the gap between the two cDNA contigs, RT-PCR was performed on fetal brain, fetal liver and adult skeletal muscle mRNA using primers derived from end sequences of contigs 5 and 6. This amplified a 820 bp product. Sequence analysis of this RT-PCR fragment indicates that it matches genomic sequence between contig 5 and 6 and confirms that these 2 contigs are part of the same gene. A 450 bp 5' rapid amplification of cDNA ends (5' RACE) fragment was generated using primer designed from contig 6. The sequence of the 5' RACE fragment matched the corresponding genomic sequence and allowed us to position the 5' end of DGS-C in the proximal portion of cosmid 4. The complete 4472 bp expressed sequence of DGS-C was assembled (Gong et al., unpublished). DGS-C also corresponds to the recently reported DGCR2/IDD gene (Demczuk et al., 1995 and Wadey et al., 1995 respectively) and identifies numerous ESTs in dBEST (Table 2 and Budarf et al., 1995). The database search for homology to known proteins revealed matches with Cys-rich related proteins, such as low-density lipoprotein receptor (LDLR), murine AM2 receptor, alpha-2-macroglobulin receptor and mouse perlecan.

DGS-D, -E and -F were assembled by contigs 7, 8 and 9, respectively. The cDNAs in contigs 7 and 8 as well as in contig 6, were initially grouped together because all three were identified by same two cosmids, cosmids 1 and 2, indicating that they mapped to the overlapping region of these two cosmids. However, the cDNAs from contig 6 could not be linked to those from contig 7 or contig 8 by hybridization of cDNA clones. Contig 9 was identified only by cosmid 4 and therefore mapped to the non-overlapping region between cosmid 3 and 5. Subsequent sequence analysis of these cDNA clones and comparison to the cosmid sequence showed that contig 7 represents sequence from within the intron between exon 7 and exon 8 of DGS-C, contig 8 lies within the intron between exon 5 and exon 6, and contig 9 is located in the first intron of the same gene (FIG. 2D). As shown in Table 2, contigs 7, 8 and 9 recognize transcripts of different size and tissue distribution, indicating that they represent three independent genes (DGS-D, -E and -F). DGS-D contains a polyadenylation signal followed by a poly(A) tail, which allowed us to orient this transcript from telomere to centromere (FIG. 2D), the same direction as DGS-C. One EST match (F04376) derived from fetal brain was obtained by searching the GenBank EST database. DGS-E was represented by contig 8 consisting of two cDNA fragments, c5G9 and c4E5, which were derived from skeletal muscle. DGS-F was represented by contig 9 containing a single cDNA, 3G11, derived from fetal brain. No significant similarity to known genes or proteins were identified by sequence analysis of the two transcripts. Because the sequences of DGS-E and -F are the same in genomic as in cDNA and did not contain a polyadenylation signal, they could represent amplified genomic DNA resulting from genomic contamination in the initial mRNA. Thus, RT-PCR was carried out on fetal brain, fetal liver and skeletal muscle mRNA. Single PCR products of the expected size were generated using primers designed from c5G9 and c3G11 (22-cSTS 5 and 6, Table 3) respectively, indicating that DGS-E and DGS-F are expressed.

In the central portion of the 250 kb region, we identified 4 genes, DGS-G, -H, -I and -J. DGS-G was assembled from the 16 cDNAs in contig 10. Eight of the clones were derived from fetal brain, 7 from skeletal muscle and one from fetal liver. Three of the DGS-G cDNAs were positive for a 0.6 kb RT-PCR product, TK (Table 1), which was generated using primers designed from GRAIL predicted exons (Uberbacher and Mural, incorporated herein by reference); E. Goldmuntz et al., unpublished). On northern blot analysis, DGS-G recognizes a 1.8 kb mRNA in testis mRNA only (FIG. 1). The nucleotide and amino acid sequences were searched using BLASTN and BLASTP, and a match was obtained with mus musculus serine/threonine kinase, but no EST was found for this transcript.

DGS-H was assembled by contig 11, which consists of 3 skeletal muscle-derived cDNAs. These recognize a 1.2 kb message in skeletal muscle and heart. We assembled a 1145 bp intronless cDNA sequence. Further, the results from the cDNA-selection experiments of DGS-H agree with sequence data obtained from cDNA clones screened from a skeletal muscle cDNA library (Clontech). No significant homologies were found to any sequences in the databases.

DGS-I was assembled from 12 skeletal muscle-derived cDNA fragments in contig 12. Two transcripts were identified, one is 1.6 kb in size expressed in all tissues, and the other is 5.2 kb expressed only in skeletal muscle and heart (FIG. 1). Five EST matches were identified in GenBank dbEST (Table 2). A database search for homology to known proteins revealed a match with a *C. elegans* hypothetical 58.3 kD protein F42H10.7 (Accession No. p34420; *Nature* 1994, 368, 32–38, 1994).

The fourth gene in this area is DGS-J represented by contig 13. This contig consists of 18 cDNA clones derived from fetal brain and skeletal muscle. Nine of the cDNAs are positive for an RT-PCR product, TP, previously mapped to this region of the mDGCR (E. Goldmuntz et al., unpublished) (Table 1). Using two clones from this contig as probes, a 1.8 kb transcript was recognized in all tissues, with very low level expression in skeletal muscle (FIG. 1). Sequence analysis showed that DGS-J has a high level of homology with a rat tricarboxylate transport protein mRNA. Sixteen ESTs derived from fetal brain, fetal liver, placenta, breast, ovary, and spleen show matches to the sequence of DGS-J (Table 2), indicating that this gene is abundantly expressed. Alternative splicing was found in two of the cDNAs selected from the skeletal muscle source. As a result of alternative splicing, the skeletal muscle transcript contains 9 exons instead of the 8 exons found in the cDNA clone identified from a fetal brain cDNA library (E. Goldmuntz et al., unpublished).

In the distal portion of the 250 kb mDGCR, we found only one gene, DGS-K, which extends over 80 kb of genomic DNA. DGS-K was assembled by cDNA contigs 14 and 15, and RT-PCR products between the two contigs. Contig 14 contains the cDNA N25-WA which has a 3.36 kb insert (Emanuel et al., 1993) and was isolated from a fetal brain cDNA library using an N25 positive cosmid as probe. Hybridization of the N25-WA cDNA to the sublibrary identified 24 positive cDNAs (Table 1). Contig 15 consists of 5 cDNAs of fetal brain origin. These two contigs recognize a transcript which is 5.5 kb in length and expressed only in adult skeletal muscle. Using primers from end sequences of contigs 14 and 15, a 1.3 kb fragment was amplified from fetal brain, fetal liver and adult skeletal muscle mRNA. The PCR product recognizes a 5.5 kb transcript in mRNA from skeletal muscle only. Comparison between the sequence of the PCR product and the corresponding genomic DNA confirmed that this RT-PCR fragment joins contigs 14 and 15. Further, using this 1.3 kb fragment we isolated 11 additional clones from the cDNA sublibrary, which were not initially detected by hybridization of cosmid 7 DNA to the arrayed cDNAs. Sequence analysis of DGS-K demonstrates it has a high degree of similarity with rat clathrin heavy chain mRNA.

Contig 16 consists of 3 cDNA clones derived from fetal brain. Each of these cDNAs was utilized as a hybridization probe against multiple tissue northern blots, and all failed to detect a transcript. However, a 146 bp PCR product was amplified from adult skeletal muscle mRNA with primers derived from cDNA 2A5 from this contig (22-cSTS13, Table 3). In order to determine whether cDNA clones from contig 16 are derived from the DGS-K gene, RT-PCR was carried out using primers designed from end sequences of contigs 15 and 16. A 500 bp fragment was generated from adult skeletal muscle mRNA. Using this PCR product as probe, a 5 KB EcoRl/Hind III fragment from cosmid 7 was identified (data not shown). The sequence of the PCR product showed high degree of homology (95%) with EST 69170 (T34493) but low identity to the corresponding cosmid sequence. We hybridized this probe to genomic DNA from a panel of monochromosomal somatic cell hybrids, and the results indicate that the RT-PCR product maps to chromosome 11 (data not shown). Thus, the cDNAs from contig 16 are not derived from DGS-K, or from chromosome 22 and there must be sequences present on chromosome 11 with homology to chromosome 22.

EXAMPLE 2

Orientation of Transcripts DGS-A through DGS-K in the mDGCR

The size and tissue distribution of the 11 transcripts we have identified are different from one another. These data suggest that there are a minimum of 11 genes present in the 250 kb we have designated the mDGCR. Fortunately, the entire genomic sequence of this region is now available for analysis. Sequence analysis of the cDNAs and the corresponding genomic DNA allowed us to establish the direction of transcription. Several methods are available to identify the sense strand of a gene. These include: 1) searching for a poly(A) tail or polyadenylation signal in the cDNA sequence, 2) analysis for presence of consensus sequences at splice junctions in the genomic DNA and 3) comparison of the new cDNAs to the orientation of known genes with which they share a high degree of homology. We have used a combination of these methods in our analysis.

Two partial cDNAs, Lan and N25-WA had previously been completely sequenced. The sequences demonstrate poly(A) tails in the centromeric end of both cDNAs, indicating that these genes (DGS-C and DGS-K) are arranged from telomere to the centromere. The poly(A) tail present in the sequence of DGS-A indicates its orientation as being centromere to telomere. The sequences of the remaining cDNAs fail to show either polyadenylation signal sequences or a poly(A) tail.

The consensus splice sites (c/a)ag*gt(a/g)agt . . . ncag*g (t/a) found in the sequences of the DGS-C, -D, -I, -J and -K indicate the direction of transcription of these genes as being form telomere to centromere. The partial sequences of DGS-B, -E, -F, -G and -H are devoid of introns, indicating that they could be intronless genes or 3' or 5' flanking sequences. In these cases, 3'-rapid amplification of cDNA ends (3' RACE) was performed using primers derived from the cDNA contigs. Sequence of the 3' RACE fragments of DGS-G showed a poly (A) signal and a poly(A) tail, indicating it is oriented from centromere to telomere as shown in FIG. 3. In addition, 3' RACE fragments of DGS-D, -I an -K were also generated, which confirmed the orientation of the transcripts which had been predicted by the presence of consensus splice sites.

Identification of expressed sequences from a defined genomic region of biological interest has been a major step in the isolation of genes involved in the etiology of genetic diseases. Two approaches, exon trapping and cDNA-selection, have recently been developed and widely applied to achieve this goal. Exon trapping is a reliable method, which permits the identification of exons, regardless of their presence in cDNA libraries (Hamaguchi, M. 1992), Duyk G M 1990, Church D M, 1994). However, false positive trapped exons result from cryptic splice sites complicating further analysis. Furthermore, in order to construct a complete transcript map, it seems unavoidable to use the trapped exons as probes to screen cDNA libraries.

In contrast, cDNA selection allows for the direct isolation of cDNAs from a genomic region of interest (Morgan, J. G. 1992, Tagle D. A. 1993, both incorporated herein by reference).

Since the starting of cDNAs can be derived from different tissues and enriched by PCR-amplification, it permits the detection of low abundant mRNAs, present at levels of 1 in 106 transcripts. For example, using the partial cDNA, LAN, as a positive control we identified 24 positive cDNAs from the cDNA sublibrary. In contrast, LAN was the only unique positive clone isolated from a fetal brain cDNA library consisting of 106 recombinant clones. It indicates that the cDNAs in the cDNA sublibrary were approximately 2000-fold enriched. However, if a gene is expressed only transiently, it is difficult to isolate by this approach. An example is the recently reported DGCR3 gene (Budarf M., et al., 1995). This gene was identified by RT-PCR of skeletal muscle cDNA using primers derived from a "trapped exon" and a GRAIL predicted exon. Using this 429 bp PCR fragment to screen our cDNA sublibrary and several conventional cDNA libraries, no positive cDNAs have been identified. These results suggest that this gene may be expressed transiently or is somehow too unstable to be cloned.

Because cDNAs from different tissues were amplified using primers derived from 3 different linkers (see method), it is useful to distinguish the source of any given selected cDNA clones by analyzing sequences of cDNAs or by PCR-amplification with corresponding primers. Of 482 selected cDNAs, nearly one half of them were derived from adult skeletal muscle. The results suggested that the transcripts present in the 250 kb region may be more abundant in skeletal muscle. based on the Northern analysis data, one transcript detected was expressed only in skeletal muscle, and four transcripts were more highly expressed in skeletal muscle than other tissues.

An additional advantage of this approach is high specificity of the constructed cDNA sublibrary. Approximately 84.6% of cDNA clones (482/570) were mapped back into the cosmid contig, and 94.8% of sequenced clones were confirmed to be derived from the corresponding genomic sequences. Only four clones (0.8%) contain Alu repeats. Because a member of the Alu family of intermediated repeats is present in 10% of cDNAs from conventional cDNA library, it tends to complicate gene identification (Levett, M. 1994). Our results indicated that this problem can be easily solved by using the human Cot-1 DNA and shared placental DNA at every step during the hybridization-based selection procedure to successfully suppress the cross-hybridization to the human repetitive sequences. Another complication arises due to mitochondrial cDNAs, which are present in all cDNA libraries. In the present study, we found two mitochondrial cDNA clones. Because the contamination of E. Coli genomic DNA in cosmid DNA may occur in the cosmid DNA preparation procedure, the mitochondrial cDNAs may be selected by using the contaminated cosmid DNA. This problem can be overcome by purification of cosmid DNA.

The direct cDNA selection approach is based on hybridization. Therefore, the cDNAs containing homologous sequences to the mDGCR can be selected, resulting in the isolation of both genes and pseudogenes. On one hand, it may complicate the isolation of candidate gene(s) involved in DGS/VCFS. On the other hand, establishing a detailed and complete transexpressed sequenceg all transcribed expressed sequences in the mDGCR will facilitate an understanding of the genomic structure and function of this biologically and medically important region.

We initially identified a minimum of 11 genes in the 250 kb of mDGCR using a direct cDNA selection-based approach, indicating that this region has a high density of genes, an average of one gene every 20–25 kb genomic sequence. These genes can be classified into two groups, tissue-specific genes such as DGS-G, -H, -I, and -K, and housekeeping genes such as DGS-C and DGS-J.

Tissue-specific and developmentally regulated expression of genes is the basic mechanism of the developmental differentiation in multicellular eukaryotes (C Helly, et al., 1989). DGS-G and DGS-K are two tissue-specific genes. DGS-G recognized a transcript only from testis, while DGS-K identified a transcript only from skeletal muscle. Both genes encode interesting proteins predicted by their homologies to mus muscular serien/threonine kinase and rat clathrin heavy chain mRNA, respectively.

DGS-H and DGS-I are two adjacent genes. They recognized transcripts, especially highly expressed in heart and skeletal muscle. The tissue-specific expression of these genes make them attractive candidated for DGS/VCFS. Housekeeping genes are usually expressed in essentially all cells and encode common structural proteins or ubiquitous enzymes (Maniatis, T. et al., 1987). In the present study, DGS-C and DGS-J are widely expressed in 16 tissues tested on Northern blot, although the expression level is not even. DGS-C is less abundant in liver, while DGS-J is more less abundant in skeletal muscle. Numerous EST matches derived from different tissues were identified with both genes, confirming their high abundance. These features are consistent with those of a typical housekeeping gene. However, some housekeeping genes also play important roles in the pathogenesis of related disorders. As an example, the recently reported SMN gene is a widely expressed gene, but the mutations and small deletions of this gene have been detected in the spinal muscular atrophy (SMA) patients, which strongly suggests that the SMN is a SMA-determining gene (Lefevre S. et al., 1995). DGS-C has been considered a candidate gene because of its position and an encoded putative member-related protein (Demczuk et al, 1995 and Wadey et al., 1995). But, so far, no mutations of DGS-C have been detected in the non-deleted DGS/VCFS patients. DGS-J is also abundantly expressed and shares a high level of homology with a rat tricarboxylate transport protein mRNA. The function of DGS-J is unknown.

EXAMPLE 3

Identification of GSCL

Identification of this gene required a sequence-driven approach, as it was not detected by any of the previous experimental methods we used, including cDNA selection, exon-amplification and direct screening of cDNA libraries. The methods were as follows.

Cosmic isolation and sequencing

A gridded 22-only library (LL22NC03) was screened by colony hybridization using a unique, genomic 2.5-KB HindIII fragment that had been subcloned from a NotI linking clone, N25. Cosmid 79 h 12 was selected for sequence analysis. The cosmid was sequenced by a double-stranded random shotgun approach (Bodenteich et al. 1993). The non-Alu sequences were searched against the DNA databases (PDB, GenBank, EMBL, emblu) with the BLASTN program (Altschul et al. 1990).

cDNA synthesis cDNA was synthesized in a 50 μl reaction using 100 ng of polyA+mRNA from various tissues. The RNA was heated with oligo(dt) primers at 65° C. for 5 minutes and allowed to cool at room temperature for 10 minutes. Reverse transcription was performed at 37° C. for 1 hour after adding 5 μl 10×1st strand buffer (Stratagene), 40 U RNase inhibitor (Stratagene), 2 μl 0.1M dNTPs and 50 U MMLV reverse transcriptase. The cDNA mixture was then heated at 90° C. for 5 minutes. For PCR amplification, 1 μl of cDNA was used per 20 μl reaction as described below.

PCR

Due to the GC-rich nature of the gene it was necessary to modify standard PCR reaction protocols by the addition of 15% glycerol or by using a high GC protocol (Dutton et al. 1993, incorporated herein by reference) with a reaction buffer containing 15% glycerol and no potassium (Woodford et al. 1995, incorporated herein by reference). In almost all cases, it was necessary to perform a nested PCR reaction or reamplification with the same primers to observe a product. This is probably due to a combination of two factors: the low abundance of the transcript and the reduced efficiency of the PCR reaction because of the high GC content of the region. The locations and sequences of the primers used are shown in FIG. 4a. Primers used were as follows:

5'ATGGCGGCAGCGGCTGGGGGCGC3' (SEQ ID NO:40)

5'CTTCAGCGAAGAGCAGCTG3' (SEQ ID NO:41)

5'TATCCTGACGTGAGTACGCG3' (SEQ ID NO:42)

5'AAATGGCGACACCAGAAGC3' (SEQ ID NO:43)

3'CCGGCGTCAAGAAGTCCCCGAAGGGG5' (SEQ ID NO:44)

5'tccctctcctgatcatccac3' (SEQ ID NO:45).

Amplification of the entire coding, region was carried out in a 20 μl reaction volume using, Vent polymerase (New England Biolabs) and a two-step PCR protocol (98° C. 1 min, 70° C. 5 min) in 15% glycerol and 75 mM Tris-Cl (pH 8.8), 20 mM (NH$_4$)2SO4, 0.1% Tween 20, 1.5 mM MgSO$_4$ (DNAmp reaction buffer). The entire reaction was analyzed on a 1% low-melt agarose gel, the resulting product was excised and 1 μl of the gel slice was reamplified using the same set of primers. Amplification between exons 2 and 3 was carried out using Taq polymerase in Taq buffer (BoehringerMannheim) in 15% glycerol at 94° C. 30 sec, 60° C. 30 sec, 72° C. 1 min. The reaction products were then diluted 1/50 and 1 μl was reamplified using, a nested set of primers. To generate the product extending from the second exon to close to the polyadenylation site, amplification was carried out using the Expand™ High Fidelity PCR System protocol (BoehringerMannheim) in 15% glycerol. The reaction products were diluted 1/50 and 1 μl was reamplified using a nested primer at the 5' end and the original primer at the 3' end.

Northern blot analysis

Multiple tissue northern blots (Clontech) were hybridized to a radiolabelled purified insert from a cloned PCR product (see text) at 65° C. in hybridization buffer as described by Church and Gilbert 1984, for 16–24 hours. Filters were washed twice in 2×SSC, 0.1% SDS at room temperature for 5 minutes and then twice in 0.1×SSC, 0.1% SDS at 65° C. for 15 minutes.

Cloning and sequencing of PCR products

PCR products were cloned using the Original TA Cloning Kit from Invitrogen. PCR products were isolated from 1% low-melting-temperature agarose and purified using the QIAquick gel purification system. Sequencing of plasmids and direct sequencing of PCR products was done on an ABI373A Sequencer.

The cosmid 79 h 12 was chosen for sequencing as part of the minimal overlap of cosmids that represent the mDGCR. When the sequence of 79 h 12 was subjected to data base searches (Altschul et al. 1990), matches to homeodomain—containing proteins were noted with the greatest similarity to goosecoid (gsc) (Blumberg et al. 1991) (see below). Based on this result, further characterization of this "goosecoid-like" gene (GSCL) was undertaken. By combining the results from database homology searches with GRAIL analysis (Uberbacher and Mural, 1991), the predicted GSCL gene structure shown in FIG. 4a was assembled. The coding region is contained within three exons and encodes a predicted protein of 205 amino acids. GSCL is a member of the paired-like class (prd-like) of homeobox genes. Similar to gsc and other members of the prd-like class of genes, the homeodomain (bold in FIG. 4a) is split by an intron between amino acids 46 and 47. Within the 60 amino acid homeodomain there is 72% identity to human goosecoid (GSC) (Blum et al. 1994) (FIG. 4b) and 71% identity to Drosophila gsc (D-gsc) (Goriely et al. 1996). By contrast, the vertebrate gsc genes have 98–100% identity to each other in this region and 76% identity to D-gsc. Based on these comparisons alone it is not possible to predict whether D-gsc represents a common ancestor to both GSC and GSCL or whether there is a second gene in Drosophila. The next most related member of the prd-like class is otxl, which has 55% identity to GSCL.

The seven most conserved amino acids in homeodomains are present in the mDGCR gene, as are six additional highly conserved amino acids, indicating that GSCL very likely encodes a functional DNA binding, protein (Burglin 1994). Like gsc, the amino acid at position 50 of the homeodomain, a residue which has been shown to be important in determining the specificity of DNA binding (Hanes and Brent 1989; Treisman et al. 1989) is a lysine (K* in FIG. 4a). Although the vast majority of homeodomains have a glutamine at this position, several homeobox genes including gsc, bicoid and orthodenticle/otx have a lysine at position 50. In general, the genes with a lysine at this position are expressed in the anterior region of the embryo.

Using an enhanced version of NCBI's BLAST search tool, BEAUTY (Worley et al. 1995), a second region of homology in the first exon was found between GSCL and gsc (bold in FIG. 4a). This region also is conserved in D-gsc (Goriely et al. 1996) and has limited similarity to the octapeptide region of Pax3 and Pax7 (Noll 1993). The extreme N-terminus of GSCL is rich in alanine, a feature which has been reported for other homeobox genes. In Drosophila, these domains have been suggested to play a role in transcriptional repression (Han and Manley 1993). Near the end of the first exon is a stretch of five cysteines. Although homopolymeric amino acid stretches are common in homeobox proteins, a stretch of Cys is novel (Burglin 1994). The homopolymeric amino acid stretches are not well conserved and their function is not clear (Burglin 1994). The predicted start codon is contained within a good consensus for translation initiation (Kozak 1986) and a TATA-like sequence is found 40 nucleotides upstream of the predicted start site of translation. In addition, there are polyadenylation signals 1967 and 1975 nucleotides beyond the predicted stop codon. Therefore, the size of the inferred transcript, including 5' and 3' UTRS, is 2.6 kb.

Figure 5A:
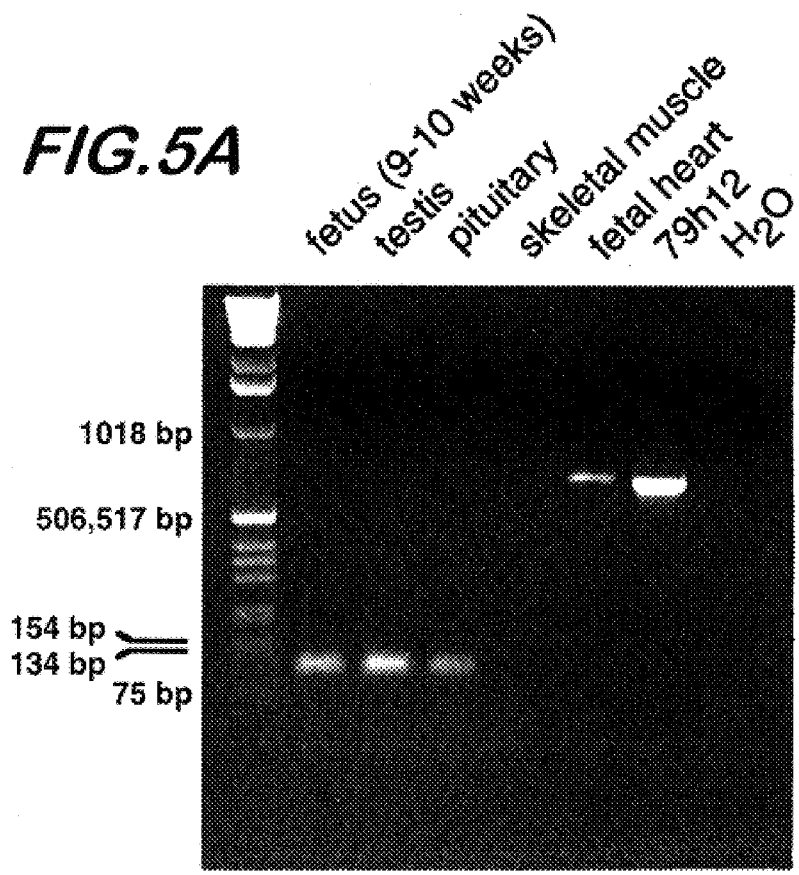
FIGS. 5a–b: Expression of GSCL. (a) Agarose gel electrophoresis of the products of PCR amplification of cDNA from various human tissue sources and the cosmid 79 h 12 using nested sets of primers between the second and third exons (see FIG. 4a). Amplification of cDNA and genomic DNA yields products of 109 and 676 bp, respectively. The band seen in fetal heart is due to genomic DNA contamination. Poly A+mRNA from 9–10 week fetal tissue was purified using the FastTrack 2.0 mRNA isolation kit from Invitrogen. (b) Multiple adult tissue Northern blot analysis (Clontech) using a cloned, purified 2050 bp cDNA probe extending from within the second exon to close to the predicted polyadenylation site. An ~2.6 kb message is detected only in testis even after a two week exposure. In addition to the blot shown here, another adult tissue Northern blot (heart, brain, placenta, lung, liver, skeletal muscle, kidney and pancreas) as well as a fetal tissue Northern blot (brain, lung, liver and kidney) were hybridized and no signal was observed.

Initial attempts to examine the expression of GSCL using a small probe derived from the genomic sequence failed to detect a signal on commercial northern blots (data not shown). Therefore, a reverse transcription-polymerase chain reaction (RT-PCR)-based assay which provides greater sensitivity, was performed. Using a forward primer beginning at the predicted start codon and a reverse primer beginning three amino acids before the stop codon (FIG. 4a), we were able to amplify a product of the expected size using polyA+mRNA from adult testis as starting material. This tissue was chosen because it has been noted to express many genes that would not necessarily be predicted to be expressed during spermatogenesis (Hecht 1995). Direct sequencing of this PCR product verified the predicted gene structure. Due to the GC-rich nature of the gene (76% across the entire coding region and 82% across the first exon), it was difficult to amplify consistently the entire coding region. Therefore, we chose a different set of primers to assay expression of GSCL in other tissues. Using primers spanning the second and third exons (FIG. 4a) we were able to detect expression in a number of tissues, including adult testis and pituitary, and 9–10 week fetal tissue (FIG. 5a). The PCR products obtained from testis and 9–10 week fetal tissue were sequenced directly confirming that the RT-PCR products represented properly-spliced GSCL transcripts. Further, to verify the use of the predicted stop codon, we amplified and sequenced a 2050 bp product from testis polyA+mRNA that extended from the second exon to 40 bp 5' of the first predicted polyadenylation signal. The sequence of this correctly-spliced product indicates that the predicted stop codon (FIG. 4a) is used.

Figure 5B:
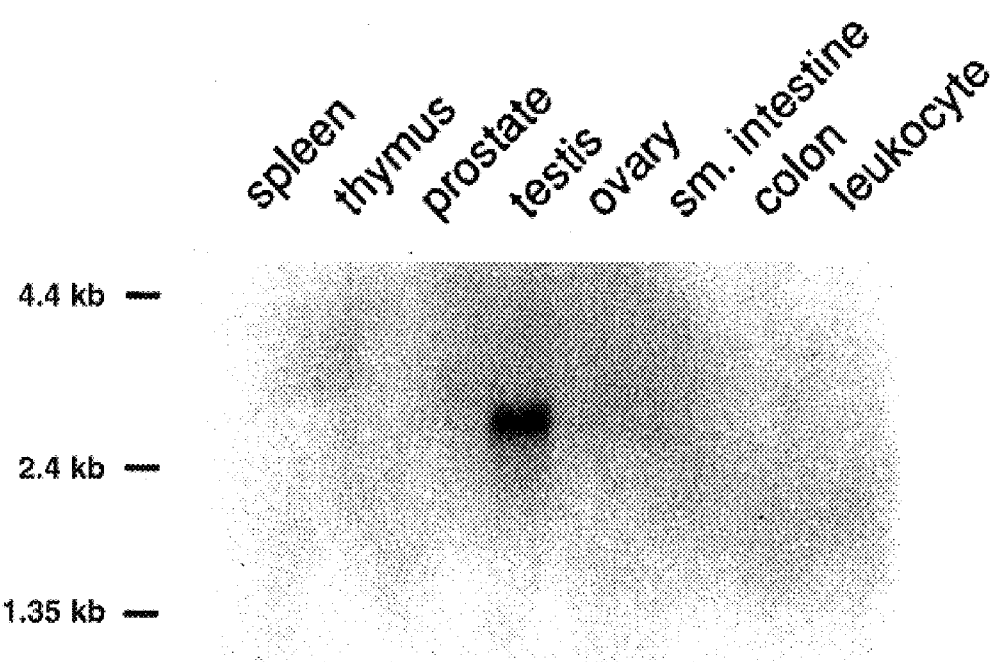

This 2050 bp PCR product was cloned and used to reprobe commercial Northern blots of fetal and adult tissues. It detected an ~2.6 KB signal in adult testis only (FIG. 5b). Expression in testis is consistent with the RT-PCR results as the amplified product was most abundant in testis. As might be predicted based on the RT-PCR results, no signal was observed in any other tissue, even after a long, exposure, suggesting that if GSCL is expressed in the other tissues represented on these blots, it must be of low abundance. The absence of a signal in 20–26 week fetal heart (the developmental state of mRNA used for the fetal Northern blot) is not surprising as the time of neural crest cell migration and aorticopulmonary septation would be completed by 7 weeks. The apparent low abundance of the message in all tissues tested, including those tested by RT-PCR, may be due to the fact that we have not yet studied those tissues in which GSCL is normally highly-expressed. In addition, the expression in testis does not necessarily suggest a role for GSCL in testis alone since there are several examples of genes that are expressed in testis but are known to be expressed in and have a function in other tissues and at other stages of development (e.g. Rubin et al. 1986; Shackleford and Varmus 1987). Taken together, these results demonstrate expression of GSCL in multiple tissues, albeit at a low level, and, notably, that GSCL is expressed during, early fetal development.

EXAMPLE 4

Mutational Analysis

Methods for detecting genetic deletions and mutations in the GSCL gene can be performed as disclosed in U.S. Pat. No. 5,576,178, hereby incorporated by reference.

Genomic DNA was available from 14 patients referred to our laboratory with a diagnosis of DGS/VCFS and no detectable deletions in 22q11. Clinical summaries were provided by either a referring- geneticist and/or immunologist. All 14 had two or more of the major clinical features seen in these disorders including congenital heart defect, absent thymus or a history of frequent infections, palatal abnormalities and/or speech difficulties, facial dysmorphia and a history of learning disabilities or developmental delay.

In the present instance, to detect point mutations and small insertions and deletions, genomic DNA from selected non-deleted patients was screened by direct sequencing of PCR products. Exons two and three were amplified independently, using primers flanking the exons, and sequenced as described above. Due to the extremely GC-rich nature of the first exon and promoter region—greater than 80% GC—we have not been able yet to obtain sequence information on this exon.

To assay for larger deletions, insertions and rearrangements within the GSCL gene, we analyzed genomic DNA from the non-deleted patients by Southern blotting analysis. Genomic DNA was digested with the restriction endonuclease PstI, separated on a 0.8% agarose gel and transferred to Hybond $N^+$ (Amersham). Blots were hybridized simultaneously with two different cloned probes. One probe contained genomic DNA from the GSCL locus beginning within the second exon and extending 70 bp beyond the stop codon. The second probe, pH20 (D22S41), was a genomic fragment from a more telomeric locus on chromosome 22 (Budarf et al. 1996). In both cases the genomic fragments were purified from a plasmid, radiolabelled and hybridized at 65° C. in hybridization buffer as described by Church and Gilbert 1984, for 16–24 hours. Filters were washed twice in 2×SSC, 0.1% SDS at room temperature for 5 minutes and then twice in 0.5×SSC, 0.1% SDS at 65° C. for 15 minutes. To determine whether there was a deletion of the locus the relative intensities of the bands from the two loci were compared using a phosphoimager.

The foregoing examples are meant to illustrate the invention, not limit it in any way. Those of ordinary skill in the art will recognize modifications within the spirit and scope of the invention as set forth in the appended claims.

References

Buckler, A. J., Chang, D. D., Graw, S. L., Brook J. D., Haber, D. A., Sharp, P. A. and Housman, D. E., (1991), Exon amplification; a strategy to isolate mammalian genes based on RNA splicing, *Proc. Nat'l Acad. Sci. USA*, 89, 4005–4009.

Church, D. M., Stotler, C. J., Rutter, J. L., Murrell, J. R., Trofatter, J. A., Buckler, A. J. (1994), Isolation of genes from complex sources of mammalian genomic DNA using exon amplification. *Nature Genet,* 6: 98–105.

Demczuk, S., Aledo, R., Zucman, J., Delatre, O., Desmaze, C., Dauphinot, L., Jalbert, Pl, Rouleau, G. A., Thomas, G. and Aurias, A., (1995), Cloning of a balanced translocation breakpoint in the DiGeorge syndrome critical region and isolation of a novel potential adhesion receptor gene in its vicinity, *Hum. Mol. Genet,* 4: 551–558.

Driscoll, D. A., Salvin, J., Sellinger, Bl, Budaft, M. L., McDonald-McGinn, D. M., Zackai, E. H., Emanuel, B. S., (1993), Prevalence of 22q11 microdeletions in DeGeorge and velocardiofacial syndromes; implications for genetic counselling and prenatal diagnosis, *J. Med. Genet.,* 30: 813–817.

Feinberg, A. P., and Vogelstein, B., (1983), A technique for radiolabeling DNA restriction endonuclease fragments to high specific activity, *Anal. Biochem.,* 132: 6–13.

Hamaguchi, M., Sakamoto, H., Tsuruta, H., Sasaki, H., Muto, T., Sugimura, T., and Terada, M., (1992), Establishment of a highly sensitive and specific exon-trapping system, *Proc. Natl. Acad. Sci. USA,* 89: 9779–9783.

Halford, S., Wilson, D. I., Daw, S. C. M., Roberts, C., Wadey, R., Kamath, S., Wickremasinghe, A., Burn, J., Goodship, J., Mattel, M. G., Moormon, A. F. M., and Scambler, P. J., (1993), Isolation of a gene expressed during early embryogenesis from the region of 22q11 commonly deleted in DiGeorge syndrome, *Hum. Mol. Genet.,* 2: 2099–2107.

Korn, B., Sedlacek, Z., Manca, A., Kioschis, P., Lehrach, H., and Poustka A., (1992), *Hum. Mol. Genet.,* 1: 235–242.

Li, M., Budart, M. L., Sellinger, B., Jaquez, M., Matalon, R., Ball, S., Pagon, R. A., Rosengren, S. S., Emanuel, B. S., Driscoll, D.A. (1994), Narrowing the DiGeorge region (DGCR) using DGS-VCFS associated translocation breakpoints. *The American J. of Hum. Genet.,* 55: A10.

Stevens, C. A., Carey, J. C., Shigeoka, A. O., *DiGeorge anomaly and Velo-Cardio-Facial syndrome*, Pediatr. 1990, 85: 526–530.

Kirby, M. L. and Bockman, D. E., Neural crest and normal development: A new perspective, *Anat. Rec.* 209: 1–6 (1984).

Altschul S F, Gish W, Miller W, Myers E W, Lipman D J (1990) Basic local alignment search tool. *J Mol Biol* 215: 403–410

Augusseau S, Jouk S, Jalbert P, Prieur M (1986) DiGeorge syndrome and 22q11 rearrangements. *Hum Genet* 74: 206

Blum M, Gaunt S J, Cho K W Y, Steinbeisser H, Blumberg, B, Bittner D, De Robertis E M (1992) Gastrulation in the Mouse: The role of the homeobox gene goosecoid. *Cell* 69: 1097–1106

Blum M, De Robertis E M, Kojis T, Heinzmann C, Klisak I, Geissert D, Sparkes RS (I 994) Molecular cloning, of the human homeobox gene goosecoid (GSC) and mapping of the gene to human chromosome 14q32. 1. *Genomics* 21: 388–393

Blumberg, B, Wright C V E, De Robertis E M, Cho K W Y (1991) Organizer-specific homeobox genes in *Xenopus laevis* embryos. *Science* 253: 194–196

Bodenteich A, Chissoe S, Wang Y., Roe B A (1993) Shotgun cloning as the strategy of choice to generate templates for high-throughput dideoxynucleotide sequencing. In: Venter J C (ed) Automated DNA Sequencing and Analysis Techniques, Academic Press, London, pp 42–50

Bruneill S, Faiella A, Capra V, Nigro V, Simeone A, Cama A, Boncinelli E (1996) Germline mutations in the homeobox gene EMX2 in patients with severe chizencephaly. *Nature Genetics* 12: 94–96

Budarf M L, Collins J, Gong W, Roe B, Wang Z, Bailey L C, Sellinger B, et al. (1995) Cloning a balanced translocation associated with DiGeorge syndrome and identification of a disrupted candidate cyene. *Nature Genetics* 10: 269–288

Budarf M L, Eckman B, Michaud D, McDonald T, Gavigan S, Buetow K H, Tatsumara Y, et al. (1996) Regional localization of over 300 loci on human chromosome 22 using, a somatic cell hybrid mapping- panel. *Genomics* 35: 275–288

Burglin T R (1994) A comprehensive classification of homeobox genes. In: Duboule D (ed) Guidebook to the homeobox genes, A Sambrook & Tooze Publication at Oxford University Press, pp 27–71

Carey A H, Kelly D, Halford S, Wadey R, Wilson D, Goodship J, Bum J, et al. (1992) Molecular genetic study of the frequency of monosomy 22q11 in DiGeorge syndrome. *Am J Hum Genet* 51: 964–970

Chisaka O, Capecchi MR (1991) Regionally restricted developmental defects resulting from targeted disruption of the mouse homeobox gene hox-1.5. *Nature* 350: 473–479

Church G M, Gilbert W (I 984) Genomic sequencing,. *Proc Natl. Acad Sci USA* 81: 1991–1995

Driscoll D A, Salvin J, Sellinger B, Budarf M L, McDonald-McGinn D M, Zackai E H, Emanuel B S (1993) Prevalence of 22q11 microdeletions in DiGeorge and velocardiofacial syndromes: implications for genetic counseling-and prenatal diagnosis. *J Med Genet* 30: 813–817

Driscoll DA (1994) Genetic basis of DiGeorge and velocardiofacial syndromes. *Curr Opin in Ped* 6: 702–706

Dutton C M, Paynton C, Sommer S S (1993) General method for amplifying regions of very high G+C content. *Nuc Acids Res* 21: 2953–2954

Gaunt S J, Blum M, De Robertis E M (1993) Expression of the mouse goosecoid gene during mid-embryogenesis may mark mesenchymal cell lineages in the developing head, limbs and body wall. *Development* 117: 769–778

Goldmuntz E, Wana Z, Roe B A, Budarf M L (1996) Cloning, genomic organization and chromosomal localization of human citrate transport protein to the DiGeorge/ Velocardialfacial syndrome minimal critical region. *Genomics* 33: 27–276

Gong, W, Emanuel B S, Collins J, Kim D H, Wang Z, Chen F, Zhang G et al. (1996) A transcription map of the DiGeorge and velo-cardio-facial syndrome minimal critical re-ion on 22q11. *Hum. Molec. Genet.* 5: 789–800

Goriely A, Stella M, Coffinier C, Kessler D, Mailhos C, Dessain S, Desplan C (1996) A functional homologue of goosecoid in Drosophila. *Development* 122: 1641–1660

Han K, Manley J L (1993) Functional domains of the Drosophila Engrailed protein. *EMBO J* 12: 2723–2733

Hanes S, Brent R (1989) DNA specificity of the bicoid activator protein is determined by homeodomain recognition helix residue 9. *Cell* 57: 1275–1283

Hecht N B (1995) The making, of a spermatozoon: a molecular perspective. *Developmental Genetics* 16: 95–103

Holmes S E, Sellinger B, Gong W, Collins J, Roe B, McDermid H E, Riazi M A et al. (1996) Features of VCFS in a patient with a balanced translocation interrupting a transcript within the minimal DGS/VCFS critical region. Paper presented at the American Society of Human Genetics, San Francisco, Calif., October 29–November 3

Jaquez M, Driscoll D A, Li M, Emanuel B S, Hernandez I. Jaquez F, Lembert N, et al. Unbalanced 15;22 translocation in a patient with features of both DiGeorge and velocardiofacial syndrome. Am J Med Genet (in press)

Kirby M L, Gale T F, Stewart D E (1983) Neural crest cells contribute to normal aorticopulmonary septation. *Science* 220: 1059–1061

Kirby M L, Bockman D E (1984) Neural crest and normal development: a new perspective. *Anat Rec* 209: 1–6

Kozak M (1986) Point mutations define a sequence flanking, the AUG initiatior codon that modulates translation by eukaryotic ribosomes. *Cell* 44: 283–292

Kurihara Y, Kurihara H, Suzuki H, Kodama T, Maemura K, Nagai R, Oda H, et al. (1994) Elevated blood pressure and craniofacial abnormalities in mice deficient in endothelin-1. *Nature* 368: 703–710

Kurihara Y, Kurihara H, Oda H, Maemura K, Nagai R, Ishikawa T, Yazaki Y (1995) Aortic arch malformations and ventricular septal defect in mice deficient in endothelin-1. *J Clin Invest* 96: 293–300

Kurahashi H, Nakayama T, Osugi Y, Tsuda E, Masuno M, Imaizumi K, Kamiya T et al. (1996) Deletion mapping, of 22q11 in CATCH22 syndrome: Identification of a second critical region. *Am J Hum Genet* 58: 1377–13481

Lammer E J, Opitz J M (I 986) The DiGeorge anomaly as a developmental field defect. *Am J Med Genet* 29: 113–127

Levy A, Demczuk S, Aurias A, Depetris D, Mattei M, Philip N (1995) Interstitial 22q11 microdeletion excluding the ADU breakpoint in a patient with DiGeorge syndrome. *Hum Molec Gen* 4: 2417–2419

Moss E, Wang, P P, McDonald-McGinn D M, Gerdes M, DaCosta A M, Emanuel B S, Batshaw N I L, et al. (1995) Characteristic cognitive profile in patients with a 22q11.1 deletion: verbal IQ exceeds nonverbal IQ. Paper presented at the American Society of Human Genetics, Minneapolis, Minn.

Noll M (1993) Evolution and role of Pax genes. Current Opinion in *Genetics* and *Development* 3: 595–605

Rivera-Perez J A, Mallo M, Gendron-Maguire M, Gridley T, Behringer R R (1995) goosecoid is not an essential component of the mouse gastrula organizer but is required for craniofacial and rib development. *Development* 121: 3005–3012

Rizzu P, Lindsay E A, Taylor C, O'Donnell H, Levy A, Scambler P, Baldini A (1996) Cloning, and comparative mapping- of a gene from the commonly deleted region of DiGeorge and Velocardiofacial syndromes conserved in *C. elegans*. Mammalian Genome 7: 639–643

Rubin M R, Toth L E, Patel M D, D'Eustacffo P, Nguyen-Huu M C (1986) A mouse homeo box gene is expressed in spermatocyes and embryos. *Science* 233: 663–667

Schorle H, Meter P, Buchert M, Jaenisch R, Mitchell P (1996) Transcription factor AP-2 essential for cranial closure and craniofacial development. *Nature* 381: 235–238

Shackleford G M, Varmus H E (I 987) Expression of the proto-oncogene int- 1 is restricted to postmeiotic male germ cells and the neural tube of mid-gestational embryos. *Cell* 50: 89–95

Treisman J, Gonczy P, Vashishtha M, Harris E, Desplan C (1989) A single amino acid can determine the DNA binding specificity of homeodomain proteins. *Cell* 59: 553–562

Uberbacher E C, Mural R L (I 991) Locating- protein-coding regions in human DNA sequences by a multiple sensor-neural network approach. *Proc Natl Acad Sci USA* 88: 11261–11265

Woodford K, Weltzmann M N, Usdin K (1995) The use of K+-free buffers eliminates a common cause of premature chain termination in PCR and PCR sequencing. *Nuc Acids Res* 23: 539

Worley K C, Wiese B A, Smith R F (1995) BEAUTY: An enhanced BLAST-based search tool that integrates multiple biological information resources into sequence similarity search results. *Genome Res* 5: 173–187

Yamada G, Mansouri A, Torres M, Stuart E T, Blum M, Schultz M, De Robertis E M, et al. (1995) Targeted mutation of the murine goosecoid gene results in craniofacial defects and neonatal death. *Development* 121: 2917–2922

Zhang, J, Hagopian-Donaldson S, Serbedzija G, Elsemore J, Plehn-Dujowich D, McMahon A P, Flavell R A, et al. (1996) Neural tube, skeletal and body wall defects in mice lacking transcription factor AP-2. *Nature* 381: 241

TABLE 1

Probes used for the analysis of cDNA sublibrary

| Probe | Size (kb) | Origin | No. of cDNAs | Reference |
|---|---|---|---|---|
| LAN | 2.4 | fetal brain cDNA library | 24 | M. Budarf, et al. (1995) |
| N25-WA | 3.36 | fetal brain cDNA library | 24 | B. Emanuel, et al (1993) |
| STK | 0.6 | RT-PCR product | 3 | E. Goldmuntz and M. Budarf (unpublished) |
| CTP | 0.6 | RT-PCR product | 6 | E. Goldmuntz and M. Budarf (unpublished) |

TABLE 2

Analysis of transcripts in the mDGCR

| Transcript | polyadenylation signal | Size (kb) of Transcript | Tissue specifity of expressed sequence | Assembled by cDNA contigs | Similarity |
|---|---|---|---|---|---|
| DGS-A | AATAAA | — | RT-PCR from skeletal | contig 1 | EST Z42407, Z38613, R19565, R38591 H17163, H17948 |
| DGS-B | unknown | 1.5 | all tissues, especially highly in heart and skeletal muscle | contig 2 contig 3 ? contig 4 ? | unknown |
| DGS-C | AATAAA | 4.5 | all tissues tested muscle and brain | contig 5,6 | 45 ESTs such as H41480, H19994, H40233 H27860, H43590, H39205, H45536, H42939 H45563, R73309, H40232, H12814, R72407 R54510, H15777, H42934, H42970, H42972 |
| DGS-D | AATAAA | 1.6, 4.0 | all tissues tested | contig 7 | EST F04376 |
| DGS-E | unknown | 1.35, 1.6 2.0 | all tissues tested liver | contig 8 | unknown |
| DGS-F | unknown | 1.8 2.6 | all tissues tested all tissues, but low expression | contig 9 | unknown |
| DGS-G | AATAAA | 1.8 | testis | contig 10 | mus musculus serine threonine kinase |
| DGS-H | unknown | 1.2 | skeletal muscle, heart | contig 11 | unknown |
| DGS-I | ATTAAA | 1.6 5.2 | all tissues tested skeletal muscle, heart | contig 12 | EST Z38497, F05516, R23410, R44195 H05365 |
| DGS-J | AATAAA | 1.8 | all tissues, but very low expression in skeletal muscle | contig 13 | Rat tricarboxylate transport protein 17 ESTs: T50580, F08153, R72468, H27262 R55394, H42358, H44309, R72424, R26361 R26147, H43127, H43877, T91330, R73208 T050446, T35714, R70172 |

TABLE 2-continued

Analysis of transcripts in the mDGCR

| Transcript | polyadenylation signal | Size (kb) of Transcript | Tissue specifity of expressed sequence | Assembled by cDNA contigs | Similarity |
|---|---|---|---|---|---|
| DGS-K | ATTAAA | 5.5 | skeletal muscle | contig 14,15 contig 16? | clathrin heavy chain mRNA unknown |

TABLE 3

STSs from cDNA sequences in the mDGCR

| Name | Primers | SEQ ID NO: | TH | FB | FL | ASM | Origin |
|---|---|---|---|---|---|---|---|
| 22-cSTS1 | GCACTTCTGTTCTGAGCAACC CTGAAGATTCCTGCTGAGGG | 4 5 | 276 | 276 | — | 276 | c2E9 (DGS-A) |
| 22-cSTS2 | GAGAAACATACAAATCAGGCCC ACGTGTTTACTGGAGAGTGTGA | 6 7 | 162 | 162 | — | 162 | c3B3 (DGS-B) |
| 22-cSTS3 | GTCAGGGCTTACCTCTCAG TTGCCTGATGTGGGTAACAA | 7 9 | 283 | 283 | 283 | 283 | c4E7 (Contig 3) |
| 22-cSTS4 | GAGCCATGCACAGCAATG GGCTCGCGTGTGTACATAGA | 10 11 | 620 | 620 | 620 | 620 | c5H5 (DGS-C) |
| 22-cSTS5 | CTTCTGCTGCAGGATAACTGG CACTATGGAGAGAGGAGTGCG | 12 13 | 351 | — | — | 351 | c5G9 (DGS-E) |
| 22-cSTS6 | CTCCATGCTGTCTTCCATAGTG GTAAGCCAAAACCACAATAGGC | 14 15 | 163 | 163 | 163 | 163 | c3G11 (DGS-F) |
| 22-cSTS7 | AGGATGTCCATCTCCCGAG TGCTGTGGAAATCTGTCTGTG | 16 17 | 279 | 279 | 279 | 279 | c5C4 (DGS-G) |
| 22-cSTS8 | CCCTCTGCTATAGGCACTGC CAGATGCTCAGGTACAGGCA | 18 19 | 705 | 705 | 705 | 705 | c4E8 (DGS-H) |
| 22-cSTS9 | CTTCTGTGTGCGTGTGGTG ATCAGCGTCGTCCTTGTTG | 20 21 | 273 | 273 | 273 | 273 | c4H2 (DGS-I) |
| 22-cSTS10 | CTGCATCACCTTCCCCAC CTTCAGCCCTCCTTGTTCC | 22 23 | 236 | 236 | 236 | 236 | c2C3 (DGS-J) |
| 22-cSTS11 | ACCAACCTCTGGGATTATTGG TGCCCTGTCTTACAGGCAG | 24 25 | 165 | 165 | 165 | 165 | c5F7 (DGS-K) |
| 22-cSTS12 | TCCAGTGGCTATGCAGATTG ATACGGTTCATGCAGATGCA | 26 27 | 114 | 114 | 114 | 114 | c2C2 (DGS-K) |
| 22-cSTS13 | AAGGCACAGAATGGAGGAGA ATAATTCCCATTGCCTGCAG | 28 29 | 146 | — | — | 146 | c2A5 (Contig 16) |

What is claimed is:

1. An isolated transcription unit encoded in the minimal DGS/VCFS chromosomal region designated as GSCL in FIG. 6.

2. The transcription unit of claim 1, encoding the amino acid sequence depicted in FIG. 4a SEQ ID NO:36.

3. A method of detecting genetic deletions and mutations associated with at least one condition selected from the group consisting of DiGeorge syndrome, Velocardiofacial syndrome, and cleft palate in a human patient comprising the steps of:

provinding a DNA containing test sample from said human patient;

contacting a detectably labeled nucleic acid probe, said probe being substantially complementary to GSCL as depicted in FIG. 6 with said test sample under hybridizing conditions; and detecting hybridization of said detectably labeled probe with DNA of chromosome 22;

whereby the absence of hybridization of said detectably labeled probe is diagnostic of the likelihood said human has a genetic deletion or mutation associated with at least one of DiGeorge syndrome, Velocardiofacial syndrome, and cleft palate.

4. A method of preparing diagnostic probes useful for the detection of genetic deletions, translocations, and mutations associated with at least one condition selected from the group consisting of DiGeorge Syndrome, Velocardiofacial syndrome, and cleft palate comprising the steps of:

preparing primer pairs effective to amplify a region of chromosome 22q11 encoding a transcript GSCL as depicted in FIG. 6;

synthesizing DNA substantially complementary to a region of normal human genomic DNA or cDNA by PCR amplification using said primer pairs; and isolating a probe to said region from a library containing human chromosome 22 using said substantially complementary DNA.

5. The method of claim 4 wherein said primer pairs are selected from the group consisting of

5'ATGGCGGCAGCGGCTGGGGGCGC3' (SEQ ID NO:40);

5'CTTCAGCGAAGAGCAGCTG3' (SEQ ID NO:41);

5'TATCCTGACGTGAGTACGCG3' (SEQ ID NO:42);

5'AAATGGCGACACCAGAAGC3' (SEQ ID NO:43);

3'CCGGCGTCAAGAAGTCCCCGAAGGGG5' (SEQ ID NO:44); and

5'tccctctcctgatcatccac3' (SEQ ID NO:45).

6. A diagnostic probe substantially complementary to transcript GSCL of chromosome 22q11 as depicted in FIG. 6.

7. The probe of claim 6, wherein said probe is prepared according to the method of claim 4.

8. A diagnostic kit for the detection of genetic deletions or mutations associated with at least one condition selected from the group consisting of DiGeorge syndrome, Velocardiofacial syndrome, and cleft palate comprising primer pairs effective to amplify a region of chromosome 22q11 encoding transcript GSCL as depicted in FIG. 6.

9. The kit of claim 8 wherein said primer pairs are selected from the group consisting of

5'ATGGCGGCAGCGGCTGGGGGCGC3' (SEQ ID NO:40);

5'CTTCAGCGAAGAGCAGCTG3' (SEQ ID NO:41);

5'TATCCTGACGTGAGTACGCG3' (SEQ ID NO:42);

5'AAATGGCGACACCAGAAGC3' (SEQ ID NO:43);

3'CCGGCGTCAAGAAGTCCCCGAAGGGG5' (SEQ ID NO:44); and

5'tccctctcctgatcatccac3' (SEQ ID NO:45).

10. A cDNA encoding the amino acid sequence depicted in FIG. 4a SEQ ID NO:36.

* * * * *

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CTCTAGAACT AGTGGATCCA TACG                                              24

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

CTCTAGAACT AGTGGATCAC TGG     23

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CTCTAGAACT AGTGGATCTA CCTG     24

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCACTTCTGT TCTGAGCAAC C     21

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CTGAAGATTC CTGCTGAGGG     20

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAGAAACATA CAAATCAGGC CC     22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
ACGTGTTTAC TGGAGAGTGT GA                                              22

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTCAGGGCTT ACCTGCTCAG                                                 20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTGCCTGATG TGGGTAACAA                                                 20

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GAGCCATGCA CAGCAATG                                                   18

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGCTCGCGTG TGTACATAGA                                                 20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CTTCTGCTGC AGGATAACTG G                                               21

(2) INFORMATION FOR SEQ ID NO:13:
```

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

CACTATGGAG AGAGGAGTGC G                                              21

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

CTCCATGCTG TCTTCCATAG TG                                             22

(2) INFORMATION FOR SEQ ID NO:15:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

GTAAGCCAAA ACCACAATAG GC                                             22

(2) INFORMATION FOR SEQ ID NO:16:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

AGGATGTCCA TCTCCCGAG                                                 19

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

TGCTGTGGAA ATCTGTCTGT G                                              21

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

CCCTCTGCTA TAGGCACTGC                                               20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

CAGATGCTCA GGTACAGGCA                                               20

(2) INFORMATION FOR SEQ ID NO:20:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

CTTCTGTGTG CGTGTGGTG                                                19

(2) INFORMATION FOR SEQ ID NO:21:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

ATCAGCGTCG TCCTTGTTG                                                19

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CTGCATCACC TTCCCCAC                                                 18

(2) INFORMATION FOR SEQ ID NO:23:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

```
CTTCAGCCCT CCTTGTTCC                                                    19

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

ACCAACCTCT GGGATTATTG G                                                 21

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGCCCTGTCT TACAGGCAG                                                    19

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TCCAGTGGCT ATGCAGATTG                                                   20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ATACGGTTCA TGCAGATGCA                                                   20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

AAGGCACAGA ATGGAGGAGA                                                   20

(2) INFORMATION FOR SEQ ID NO:29:
```

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:29:

ATAATTCCCA TTGCCTGCAG                                          20

(2) INFORMATION FOR SEQ ID NO:30:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Met Asp Asp Ala Thr Val Leu Arg Lys Lys Gly Tyr Ile Val Gly Ile
1               5                   10                  15

Asn Leu Gly Lys Gly Ser Tyr Ala Lys Val Lys Ser Ala Tyr Ser Glu
            20                  25                  30

Arg Leu Lys Phe Asn Val Ala Val Lys Ile Ile Asp Arg Lys Lys Thr
        35                  40                  45

Pro Thr Asp Phe Val Glu Arg Phe Leu Pro Arg Glu Met Asp Ile Leu
    50                  55                  60

Ala Thr Val Asn His Gly Ser Ile Ile Lys Thr Tyr Glu Ile Phe Glu
65                  70                  75                  80

Thr Ser Asp Gly Arg Ile Tyr Ile Ile Met Glu Leu Gly Val Gln Gly
                85                  90                  95

Asp Leu Leu Glu Phe Ile Lys Cys Gln Gly Ala Leu His Glu Asp Val
            100                 105                 110

Ala Arg Lys Met Phe Arg Gln Leu Ser Ser Ala Val Lys Tyr Cys His
        115                 120                 125

Asp Leu Asp Ile Val His Arg Asp Leu Lys Cys Glu Asn Leu Leu Leu
130                 135                 140

Asp Lys Asp Phe Asn Ile Lys Leu Ser Asp Phe Gly Phe Ser Lys Arg
145                 150                 155                 160

Cys Leu Arg Asp Ser Asn Gly Arg Ile Ile Leu Ser Lys Thr Phe Cys
                165                 170                 175

Gly Ser Ala Ala Tyr Ala Ala Pro Glu Val Leu Gln Ser Ile Pro Tyr
            180                 185                 190

Gln Pro Lys Val Tyr Asp Ile Trp Ser Leu Gly Val Ile Leu Tyr Ile
        195                 200                 205

Met Val Cys Gly Ser Met Pro Tyr Asp Asp Ser Asp Ile Arg Lys Met
    210                 215                 220

Leu Arg Ile Gln Lys Glu His Arg Val Asp Phe Pro Arg Ser Lys Asn
225                 230                 235                 240

Leu Thr Cys Glu Cys Lys Asp Leu Ile Tyr Arg Met Leu Gln Pro Asp
                245                 250                 255

Val Ser Gln Arg Leu His Ile Asp Glu Ile Leu Ser His Ser Trp Leu
            260                 265                 270

Gln (2) INFORMATION FOR SEQ ID NO:31:

(i) SEQUENCE CHARACTERISTICS:
    (A) LENGTH: 272 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:31:

```
Met Asp Asp Ala Ala Val Leu Lys Arg Arg Gly Tyr Ile Met Gly Ile
1               5                   10                  15

Asn Leu Gly Glu Gly Ser Tyr Ala Lys Val Lys Ser Ala Tyr Ser Glu
            20                  25                  30

Arg Leu Lys Phe Asn Val Ala Val Lys Ile Ile Asp Arg Lys Lys Ala
        35                  40                  45

Pro Ser Asp Phe Leu Glu Lys Phe Leu Pro Arg Glu Ile Glu Ile Leu
    50                  55                  60

Ala Met Leu Asn His Arg Ser Ile Val Lys Thr Tyr Glu Ile Phe Ala
65                  70                  75                  80

Thr Ser Asp Gly Lys Val Tyr Ile Val Met Glu Leu Gly Val Gln Gly
                85                  90                  95

Asp Leu Leu Glu Phe Ile Lys Thr Arg Gly Ala Leu Gln Glu Asp Asp
            100                 105                 110

Ala Arg Lys Lys Phe His Gln Leu Ser Ser Ala Ile Lys Tyr Cys His
        115                 120                 125

Asp Leu Asp Val Val His Arg Asp Leu Lys Ser Glu Asn Leu Leu Leu
    130                 135                 140

Asp Lys Asp Phe Asn Ile Lys Leu Ser Asp Phe Gly Phe Ser Lys Arg
145                 150                 155                 160

Cys Leu Arg Asp Asp Ser Gly Arg Leu Ile Leu Ser Lys Thr Phe Cys
                165                 170                 175

Gly Ser Ala Ala Tyr Ala Ala Pro Glu Val Leu Gln Gly Ile Pro Tyr
            180                 185                 190

Gln Pro Lys Val Tyr Asp Ile Trp Ser Leu Gly Val Ile Leu Tyr Ile
        195                 200                 205

Met Val Cys Gly Ser Met Pro Tyr Asp Asp Ser Asn Ile Lys Lys Leu
    210                 215                 220

Arg Ile Gln Lys Glu His Arg Val Asn Phe Pro Arg Ser Lys His Leu
225                 230                 235                 240

Thr Gly Glu Cys Lys Asp Leu Ile Tyr Arg Met Leu Gln Pro Asp Val
                245                 250                 255

Asn Arg Arg Leu His Ile Asp Glu Ile Leu Asn His Cys Trp Val Gln
            260                 265                 270
```

(2) INFORMATION FOR SEQ ID NO:32:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Met Pro Ala Pro Arg Ala Pro Arg Ala Leu Ala Ala Ala Ala Pro Ala
1               5                   10                  15

Ser Gly Lys Ala Lys Leu Thr His Pro Glu Lys Ala Ile Leu Ala Gly
            20                  25                  30
```

Gly Leu Ala Gly Gly Ile Glu Ile Cys Ile Thr Phe Pro Thr Glu Tyr
            35                  40                  45

Val Lys Thr Gln Leu Gln Leu Asp Glu Arg Ser His Pro Pro Arg Tyr
 50                  55                  60

Arg Gly Ile Gly Asp Cys Val Arg Gln Thr Val Arg Ser His Gly Val
 65                  70                  75                  80

Leu Gly Leu Tyr Arg Gly Leu Ser Ser Leu Leu Tyr Gly Ser Ile Pro
                85                  90                  95

Lys Ala Ala Val Arg Phe Gly Met Phe Glu Phe Leu Ser Asn His Met
                100                 105                 110

Arg Asp Ala Gln Gly Arg Leu Asp Ser Thr Arg Gly Leu Leu Cys Gly
                115                 120                 125

Leu Gly Ala Gly Val Ala Glu Ala Val Val Val Cys Pro Met Glu
        130                 135                 140

Thr Val Lys Val Lys Phe Ile His Asp Gln Thr Ser Pro Asn Pro Lys
145                 150                 155                 160

Tyr Arg Gly Phe Phe His Gly Val Arg Glu Ile Val Arg Glu Gln Gly
                165                 170                 175

Leu Lys Gly Thr Tyr Gln Gly Leu Thr Ala Thr Val Leu Lys Gln Gly
                180                 185                 190

Ser Asn Gln Ala Ile Arg Phe Val Met Thr Ser Leu Arg Asn Trp
        195                 200                 205

Tyr Arg Gly Asp Asn Pro Asn Lys Pro Met Asn Pro Leu Ile Thr Gly
210                 215                 220

Val Phe Gly Ala Ile Ala Gly Ala Ala Ser Val Phe Gly Asn Thr Pro
225                 230                 235                 240

Leu Asp Val Ile Lys Thr Arg Met Gln Gly Leu Glu Ala His Lys Tyr
                245                 250                 255

Arg Asn Thr Trp Asp Cys Gly Leu Gln Ile Leu Lys Lys Glu Gly Leu
                260                 265                 270

Lys Ala Phe Tyr Lys Gly Thr Phe Pro Arg Leu Gly Arg Val Cys Leu
                275                 280                 285

Asp Val Ala Ile Val Phe Val Ile Tyr Asp Glu Val Tyr Lys Leu Leu
                290                 295                 300

Asn Lys Val Trp Lys Thr Asp
305                 310

(2) INFORMATION FOR SEQ ID NO:33:

(i) SEQUENCE CHARACTERISTICS:
            (A) LENGTH: 311 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:33:

Met Ala Ala Pro Arg Ala Pro Arg Ala Leu Thr Ala Ala Pro Gly
 1               5                   10                  15

Ser Gly Lys Ala Lys Leu Thr His Pro Gly Lys Ala Ile Leu Ala Gly
                20                  25                  30

Gly Leu Ala Gly Gly Ile Glu Ile Cys Ile Thr Phe Pro Thr Glu Tyr
                35                  40                  45

Val Lys Thr Gln Leu Gln Leu Asp Glu Arg Ala Asn Pro Pro Arg Tyr
 50                  55                  60

-continued

```
Arg Gly Ile Gly Asp Cys Val Arg Gln Thr Val Arg Ser His Gly Val
65                  70                  75                  80

Leu Gly Leu Tyr Arg Gly Leu Ser Ser Leu Leu Tyr Gly Ser Ile Pro
                85                  90                  95

Lys Ala Ala Val Arg Phe Gly Met Phe Glu Phe Leu Ser Asn His Met
            100                 105                 110

Arg Asp Ala Gln Gly Arg Leu Asp Ser Arg Arg Gly Leu Leu Cys Gly
            115                 120                 125

Leu Gly Ala Gly Val Ala Glu Ala Val Val Val Cys Pro Met Glu
    130                 135                 140

Thr Val Lys Val Lys Phe Ile His Asp Gln Thr Ser Ser Asn Pro Lys
145                 150                 155                 160

Tyr Arg Gly Phe Phe His Gly Val Arg Glu Ile Val Arg Glu Gln Gly
                165                 170                 175

Leu Lys Gly Thr Tyr Gln Gly Leu Thr Ala Thr Val Leu Lys Gln Gly
            180                 185                 190

Ser Asn Gln Ala Ile Arg Phe Phe Val Met Thr Ser Leu Arg Asn Trp
            195                 200                 205

Tyr Gln Gly Asp Asn Pro Asn Lys Pro Met Asn Pro Leu Ile Thr Gly
    210                 215                 220

Val Phe Gly Ala Val Ala Gly Ala Ala Ser Val Phe Gly Asn Thr Pro
225                 230                 235                 240

Leu Asp Val Ile Lys Thr Arg Met Gln Gly Leu Glu Ala His Lys Tyr
                245                 250                 255

Arg Asn Thr Leu Asp Cys Gly Val Gln Ile Leu Lys Asn Glu Gly Pro
            260                 265                 270

Lys Ala Phe Tyr Lys Gly Thr Val Pro Arg Leu Gly Arg Val Cys Leu
            275                 280                 285

Asp Val Ala Ile Val Phe Val Ile Tyr Asp Glu Val Val Lys Leu Leu
    290                 295                 300

Asn Lys Val Trp Lys Thr Asp
305                 310

(2) INFORMATION FOR SEQ ID NO:34:

(i) SEQUENCE CHARACTERISTICS:
        (A) LENGTH: 871 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Glu Ala Lys Leu Thr Asp Gln Leu Pro Leu Ile Ile Val Cys Asp Arg
1               5                   10                  15

Phe Gly Phe Val His Asp Leu Val Leu Tyr Leu Tyr Arg Asn Asn Leu
                20                  25                  30

Gln Arg Tyr Ile Glu Ile Tyr Val Gln Lys Val Asn Pro Ser Arg Thr
            35                  40                  45

Pro Ala Val Ile Gly Gly Leu Leu Asp Val Asp Cys Ser Glu Glu Val
    50                  55                  60

Ile Lys His Leu Ile Met Ala Val Arg Gly Gln Phe Ser Thr Asp Glu
65                  70                  75                  80

Leu Val Ala Glu Val Glu Lys Arg Asn Arg Leu Lys Leu Leu Leu Pro
                85                  90                  95

Trp Leu Glu Ser Gln Ile Gln Glu Gly Cys Glu Glu Pro Ala Thr His
```

```
                    100                     105                     110
Asn Ala Leu Ala Lys Ile Tyr Ile Asp Ser Asn Asn Ser Pro Glu Cys
            115                     120                 125
Phe Leu Arg Glu Asn Ala Tyr Tyr Asp Ser Ser Val Val Gly Arg Tyr
        130                     135                 140
Cys Glu Lys Arg Asp Pro His Leu Ala Cys Val Ala Tyr Glu Arg Gly
145                     150                  155                     160
Gln Cys Asp Leu Glu Leu Ile Lys Val Cys Asn Glu Asn Ser Leu Phe
                165                     170                 175
Lys Ser Glu Ala Arg Tyr Leu Val Cys Arg Lys Asp Pro Glu Leu Trp
                180                     185                 190
Ala His Val Leu Glu Glu Thr Asn Pro Ser Arg Arg Gln Leu Ile Asp
        195                     200                 205
Gln Val Val Gln Thr Ala Leu Ser Glu Thr Arg Asp Pro Glu Glu Ile
        210                     215                 220
Ser Val Thr Val Lys Ala Phe Met Thr Ala Asp Leu Pro Asn Glu Leu
225                     230                     235                 240
Ile Glu Leu Leu Glu Lys Ile Val Leu Asp Asn Ser Val Phe Ser Glu
                245                     250                 255
His Arg Asn Leu Gln Asn Leu Leu Ile Leu Thr Ala Ile Lys Ala Asp
                260                     265                 270
Arg Thr Arg Val Met Glu Tyr Ile Ser Arg Leu Asp Asn Tyr Asp Ala
        275                     280                 285
Leu Asp Ile Ala Ser Ile Ala Val Ser Ser Ala Leu Tyr Glu Glu Ala
        290                     295                 300
Phe Thr Val Phe His Lys Phe Asp Met Asn Ala Ser Ala Ile Gln Val
305                     310                     315                 320
Leu Ile Glu His Ile Gly Asn Leu Asp Arg Ala Tyr Glu Phe Ala Glu
                325                     330                 335
Arg Cys Asn Glu Pro Ala Val Trp Ser Gln Leu Ala Gln Ala Gln Leu
                340                     345                 350
Gln Lys Asp Leu Val Lys Glu Ala Ile Asn Ser Tyr Ile Arg Gly Asp
        355                     360                 365
Asp Pro Ser Ser Tyr Leu Glu Val Val Gln Ser Ala Ser Arg Ser Asn
        370                     375                 380
Asn Trp Glu Asp Leu Val Lys Phe Leu Gln Met Ala Arg Lys Lys Gly
385                     390                     395                 400
Arg Glu Ser Tyr Ile Glu Thr Glu Leu Ile Phe Ala Leu Ala Lys Thr
                405                     410                 415
Ser Arg Val Ser Glu Leu Glu Asp Phe Ile Asn Gly Pro Asn Asn Ala
                420                     425                 430
His Ile Gln Gln Val Gly Asp Arg Cys Tyr Glu Glu Gly Met Tyr Glu
        435                     440                 445
Ala Ala Lys Leu Leu Tyr Ser Asn Val Ser Asn Phe Ala Arg Leu Ala
        450                     455                 460
Ser Thr Leu Val His Leu Gly Glu Tyr Gln Ala Ala Val Asp Asn Ser
465                     470                     475                 480
Arg Lys Ala Ser Ser Thr Arg Thr Trp Lys Glu Val Cys Phe Ala Cys
                485                     490                 495
Met Asp Gly Gln Glu Phe Arg Phe Ala Gln Leu Cys Gly Leu His Ile
                500                     505                 510
Val Ile His Ala Asp Glu Leu Glu Glu Leu Met Cys Tyr Tyr Gln Asp
        515                     520                 525
```

-continued

```
Arg Gly Tyr Phe Glu Glu Leu Ile Leu Leu Glu Ala Ala Leu Gly
530                 535                 540

Leu Glu Arg Ala His Met Gly Met Phe Thr Glu Leu Ala Ile Leu Tyr
545                 550                 555                 560

Ser Lys Phe Lys Pro Gly Lys Met Leu Glu His Leu Glu Leu Phe Trp
                565                 570                 575

Ser Arg Val Asn Ile Pro Lys Val Leu Arg Ala Ala Glu Gln Ala His
                580                 585                 590

Leu Trp Ala Glu Leu Val Phe Leu Tyr Asp Lys Tyr Glu Gly Tyr Asp
            595                 600                 605

Asn Ala Val Leu Thr Met Met Ser His Pro Thr Glu Ala Trp Lys Glu
610                 615                 620

Gly Gln Phe Lys Asp Ile Ile Thr Lys Val Ala Asn Val Glu Leu Cys
625                 630                 635                 640

Tyr Arg Ala Leu Gln Phe Tyr Leu Asp Tyr Lys Pro Leu Leu Ile Asn
                645                 650                 655

Asp Leu Leu Tyr Leu Ser Pro Arg Leu Asp His Thr Trp Thr Val
                660                 665                 670

Ser Phe Phe Ser Lys Ala Gly Gln Leu Pro Leu Val Lys Pro Tyr Leu
            675                 680                 685

Arg Ser Val Gln Ser His Asn Asn Lys Ser Val Asn Glu Ala Leu Asn
690                 695                 700

His Leu Leu Thr Glu Glu Asp Tyr Gln Gly Leu Arg Ala Ser Ile
705                 710                 715                 720

Asp Ala Tyr Asp Asn Phe Asp Asn Ile Ser Leu Ala Gln Gln Leu Glu
                725                 730                 735

Lys His Gln Leu Met Glu Phe Arg Cys Ile Ala Ala Tyr Leu Tyr Lys
            740                 745                 750

Gly Asn Asn Trp Trp Ala Gln Ser Val Glu Leu Cys Lys Lys Asp His
            755                 760                 765

Leu Tyr Lys Asp Ala Met Gln His Ala Ala Glu Ser Arg Asp Ala Glu
770                 775                 780

Leu Ala Gln Lys Leu Leu Gln Trp Phe Leu Glu Gly Lys Arg Glu
785                 790                 795                 800

Cys Phe Ala Ala Cys Leu Phe Thr Cys Tyr Asp Leu Leu Arg Pro Asp
                805                 810                 815

Asn Val Leu Glu Leu Ala Trp Arg His Asn Leu Val Asp Leu Ala Met
                820                 825                 830

Pro Tyr Phe Ile Gln Val Met Arg Glu Tyr Leu Ser Lys Val Asp Lys
            835                 840                 845

Leu Asp Ala Leu Glu Ser Leu Arg Lys Gln Glu Glu His Val Thr Glu
850                 855                 860

Pro Ala Pro Leu Val Phe Asp
865                 870
```

(2) INFORMATION FOR SEQ ID NO:35:

(i) SEQUENCE CHARACTERISTICS:
        (A) LENGTH: 871 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Glu Ala Lys Leu Thr Asp Gln Leu Pro Leu Ile Ile Val Cys Asp Arg

```
1               5                    10                   15
Phe Asp Phe Val His Asp Leu Val Leu Tyr Leu Tyr Arg Asn Asn Leu
                20                  25                  30
Gln Lys Tyr Ile Glu Ile Tyr Val Gln Lys Val Asn Pro Ser Arg Leu
                35                  40                  45
Pro Val Val Ile Gly Gly Leu Leu Asp Val Asp Cys Ser Glu Asp Val
                50                  55                  60
Ile Lys Asn Leu Ile Leu Val Val Arg Gly Gln Phe Ser Thr Asp Glu
65                              70                  75                  80
Leu Val Ala Glu Val Glu Lys Arg Asn Arg Leu Lys Leu Leu Leu Pro
                        85                  90                  95
Trp Leu Glu Ala Arg Ile His Glu Gly Cys Glu Glu Pro Ala Thr His
                        100                 105                 110
Asn Ala Leu Ala Lys Ile Tyr Ile Asp Ser Asn Asn Asn Pro Glu Arg
                        115                 120                 125
Phe Leu Arg Glu Asn Pro Tyr Tyr Asp Ser Arg Val Val Gly Lys Tyr
                        130                 135                 140
Cys Glu Lys Arg Asp Pro His Leu Ala Cys Val Ala Tyr Glu Arg Gly
145                     150                 155                 160
Gln Cys Asp Leu Glu Leu Ile Asn Val Cys Asn Glu Asn Ser Leu Phe
                        165                 170                 175
Lys Ser Leu Ser Arg Tyr Leu Val Arg Arg Lys Asp Pro Glu Leu Trp
                        180                 185                 190
Gly Ser Val Leu Leu Glu Ser Asn Pro Tyr Arg Arg Pro Leu Ile Asp
                        195                 200                 205
Gln Val Val Gln Thr Ala Leu Ser Glu Thr Gln Asp Pro Glu Glu Val
                        210                 215                 220
Ser Val Thr Val Lys Ala Phe Met Thr Ala Asp Leu Pro Asn Glu Leu
225                     230                 235                 240
Ile Glu Leu Leu Glu Lys Ile Val Leu Asp Asn Ser Val Phe Ser Glu
                        245                 250                 255
His Arg Asn Leu Gln Asn Leu Leu Ile Leu Thr Ala Ile Lys Ala Asp
                        260                 265                 270
Arg Thr Arg Val Met Glu Tyr Ile Asn Arg Leu Asp Asn Tyr Asp Ala
                        275                 280                 285
Pro Asp Ile Ala Asn Ile Ala Ile Ser Asn Glu Leu Phe Glu Glu Ala
                        290                 295                 300
Phe Ala Ile Phe Arg Lys Phe Asp Val Asn Thr Ser Ala Val Gln Val
305                     310                 315                 320
Leu Ile Glu His Ile Gly Asn Leu Asp Arg Ala Tyr Glu Phe Ala Glu
                        325                 330                 335
Arg Cys Asn Glu Pro Ala Val Trp Ser Gln Leu Ala Lys Ala Gln Leu
                        340                 345                 350
Gln Lys Gly Met Val Lys Glu Ala Ile Asp Ser Tyr Ile Lys Ala Asp
                        355                 360                 365
Asp Pro Ser Ser Tyr Met Glu Val Val Gln Ala Ala Asn Thr Ser Gly
                        370                 375                 380
Asn Trp Glu Glu Leu Val Lys Tyr Leu Gln Met Ala Arg Lys Lys Ala
385                     390                 395                 400
Arg Glu Ser Tyr Val Glu Thr Glu Leu Ile Phe Ala Leu Ala Lys Thr
                        405                 410                 415
Asn Arg Leu Ala Glu Leu Glu Glu Phe Ile Asn Gly Pro Asn Asn Ala
                        420                 425                 430
```

-continued

```
His Ile Gln Gln Val Gly Asp Arg Cys Tyr Asp Glu Lys Met Tyr Asp
            435                 440                 445

Ala Ala Lys Leu Leu Tyr Asn Asn Val Ser Asn Phe Gly Arg Leu Ala
            450                 455                 460

Ser Thr Leu Val His Leu Gly Glu Tyr Gln Ala Val Asp Gly Ala
465                 470                 475                 480

Arg Lys Ala Asn Ser Thr Arg Thr Trp Lys Glu Val Cys Phe Ala Cys
                    485                 490                 495

Val Asp Gly Lys Glu Phe Arg Leu Ala Gln Met Cys Gly Leu His Ile
                500                 505                 510

Val Val His Ala Asp Glu Leu Glu Glu Leu Ile Asn Tyr Tyr Gln Asp
            515                 520                 525

Arg Gly Tyr Phe Glu Glu Leu Ile Thr Met Leu Glu Ala Ala Leu Gly
530                 535                 540

Leu Glu Arg Ala His Met Gly Met Phe Thr Glu Leu Ala Ile Leu Tyr
545                 550                 555                 560

Ser Lys Phe Lys Pro Gln Lys Met Arg Glu His Leu Glu Leu Phe Trp
565                 565                 570                 575

Ser Arg Val Asn Ile Pro Lys Val Leu Arg Ala Ala Glu Gln Ala His
                580                 585                 590

Leu Trp Ala Glu Leu Val Phe Leu Tyr Asp Lys Tyr Glu Glu Tyr Asp
            595                 600                 605

Asn Ala Ile Ile Thr Met Met Asn His Pro Thr Asp Ala Trp Lys Glu
610                 615                 620

Gly Gln Phe Lys Asp Ile Ile Thr Lys Val Ala Asn Val Glu Leu Tyr
625                 630                 635                 640

Tyr Arg Ala Ile Gln Phe Tyr Asp Glu Phe Lys Pro Leu Leu Leu Asn
                645                 650                 655

Asp Leu Leu Met Val Leu Ser Pro Arg Leu Asp His Thr Arg Ala Val
            660                 665                 670

Asn Tyr Phe Ser Lys Val Lys Gln Leu Pro Leu Val Lys Pro Tyr Leu
            675                 680                 685

Arg Ser Val Gln Asn His Asn Asn Lys Ser Val Asn Glu Ser Leu Asn
            690                 695                 700

Asn Leu Phe Ile Thr Glu Glu Asp Tyr Gln Ala Leu Arg Thr Ser Ile
705                 710                 715                 720

Asp Ala Tyr Asp Asn Phe Asp Asn Ile Ser Leu Ala Gln Arg Leu Glu
                725                 730                 735

Lys His Glu Leu Ile Glu Phe Arg Arg Ile Ala Ala Tyr Leu Phe Lys
            740                 745                 750

Gly Asn Asn Arg Trp Lys Gln Ser Val Glu Leu Cys Lys Lys Asp Ser
            755                 760                 765

Leu Tyr Lys Asp Ala Met Gln Tyr Ala Ser Glu Ser Lys Asp Thr Glu
770                 775                 780

Leu Ala Glu Glu Leu Leu Gln Trp Phe Leu Gln Glu Glu Lys Arg Glu
785                 790                 795                 800

Cys Phe Gly Ala Cys Leu Phe Thr Cys Tyr Asp Leu Leu Arg Pro Asp
                805                 810                 815

Val Val Leu Glu Thr Ala Trp Arg His Asn Ile Met Asp Phe Ala Met
            820                 825                 830

Pro Tyr Phe Ile Gln Val Met Lys Glu Tyr Leu Thr Lys Val Asp Lys
            835                 840                 845

Leu Asp Ala Ser Glu Ser Leu Arg Lys Glu Glu Glu Gln Ala Thr Glu
850                 855                 860
```

```
Thr Gln Pro Ile Val Tyr Gly
865                 870

(2) INFORMATION FOR SEQ ID NO:36:

(i) SEQUENCE CHARACTERISTICS:
        (A) LENGTH: 3507 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon
        (B) LOCATION: 163..423

(ix) FEATURE:
        (A) NAME/KEY: exon
        (B) LOCATION: 532..783

(ix) FEATURE:
        (A) NAME/KEY: exon
        (B) LOCATION: 1351..1458

(ix) FEATURE:
        (A) NAME/KEY: CDS
        (B) LOCATION: join(163..423, 532..783, 1351..1458)

(xi) SEQUENCE DESCRIPTION: SEQ ID NO:36:

CCCGCGCGCG GAGGCAGGGC CGCCGCAGTC GAGGATTAGC GCGTTCGCGG CCGGCGCTGC      60

GGGATTAACC CGCGTGGACT GGACGCCCGG CCCGGGGATT ACTGCGCGCT CCCTCCCCGA     120

CGTATATATT CCCGCGGCGG CGGCGCCCCG GCCGGGCCGG GC ATG GCG GCA GCG       174
                                                Met Ala Ala Ala
                                                 1

GCT GGG GGC GCG GCG AGC CGC CGG GGT GCC GGG CGG CCC TGC CCC TTC       222
Ala Gly Gly Ala Ala Ser Arg Arg Gly Ala Gly Arg Pro Cys Pro Phe
 5              10                  15                  20

TCC ATC GAG CAC ATC CTC TCC AGC CTG CCC GAG CGG AGC CTC CCG GCC       270
Ser Ile Glu His Ile Leu Ser Ser Leu Pro Glu Arg Ser Leu Pro Ala
             25                  30                  35

CGG GCC GCC TGC CCA CCG CAG CCC GCC GGT CGC CAG AGC CCC GCG AAG       318
Arg Ala Ala Cys Pro Pro Gln Pro Ala Gly Arg Gln Ser Pro Ala Lys
         40                  45                  50

CCA GAG GAG CCC GGG GCG CCC GAG GCT GCG CCC TGC GCC TGC TGC           366
Pro Glu Glu Pro Gly Ala Pro Glu Ala Ala Pro Cys Ala Cys Cys Cys
     55                  60                  65

TGC TGC GGC CCC CGC GCG GCG CCC TGC GGG CCC CCA GAG GCG GCC GCC       414
Cys Cys Gly Pro Arg Ala Ala Pro Cys Gly Pro Pro Glu Ala Ala Ala
 70                  75                  80

GGG CTG GGT GAGTGGGCGC GGAGCGGGGC GCGGGCCCG GCGGAGCCCG                463
Gly Leu Gly
 85

GGGCGCGGCG CAGTGGGTGC CGAGCTTGGC CCCAGCCCCG CGCCTCACCG CGCCCTCGCT     523

CCGCAGGC GCT CGT CTG GCG TGG CCG CTG AGG CTG GGA CCG GCG GTG CCC      573
         Ala Arg Leu Ala Trp Pro Leu Arg Leu Gly Pro Ala Val Pro
              90                  95                 100

TTG TCT CTG GGT GCG CCA GCC GGA GGT TCC GGG GCG CTC CCG GGC GCG       621
Leu Ser Leu Gly Ala Pro Ala Gly Gly Ser Gly Ala Leu Pro Gly Ala
             105                 110                 115

GTC GGC CCG GGT TCG CAG CGG CGC ACG AGG CGC CAC CGC ACC ATC TTC       669
Val Gly Pro Gly Ser Gln Arg Arg Thr Arg Arg His Arg Thr Ile Phe
         120                 125                 130

AGC GAA GAG CAG CTG CAG GCG CTC GAG GCG CTT TTC GTG CAG AAC CAG       717
```

```
      Ser Glu Glu Gln Leu Gln Ala Leu Glu Ala Leu Phe Val Gln Asn Gln
           135                 140                 145

TAT CCT GAC GTG AGT ACG CGC GAG CGC CTG GCC GGC CGC ATC CGC CTT        765
Tyr Pro Asp Val Ser Thr Arg Glu Arg Leu Ala Gly Arg Ile Arg Leu
150                 155                 160                 165

CGC GAG GAG CGC GTG GAG GTGAGTGCCC CGCCCAGCCT TTCCCCGGAG              813
Arg Glu Glu Arg Val Glu
                170

CGCGCGGGCC GCGGCTACAC TGGACTGGGG TCCTGGCGGG CGGGCGCCCT TTGCAAAGAC     873

GGCCTCGGCC CAAGCCCCGC CCTGGCGCGC CGGAGGGAGG AGGTCCCTGG ACGGCGCTGG     933

GCGTCCGGGG GTATGAGGAG CGGGTGAGAG CAGGGAGGTG CCGCGGGAAA GGAACCGGAG     993

GGCTACTTTT CTTTTCTTTT GTTTTACACT TTCCTCTGGT GACGAAAGAG GCCCGCGTTC    1053

ACGTCCAGAA TTTGGGAAAT TCAGAAGAGC CCGCAACCCA GAAGGGGCG TCCTGGTCGC    1113

CGCCAGCTGG AGGCTGGGGC GGGTACTAAG GGGGTTCCCA TCTCGCGTCC AGACCCACCG    1173

AGTCTGTCCG CAGCGAATAA GGGCAGGTGG CGCGCAGCCG CGGCCCGGGT GTCGGCTCTA    1233

CAGCGCCGTC CGCCCACATC CCTGTTGCGA AGCTCCCCTC TCGGTCCCTG TGGGACCCTC    1293

GGGAGCCGGT GGGACGCAGG ACCTGGGGCT AGGGCTGAGC ATTCCCCCCA TCCCCAG       1350

GTC TGG TTC AAG AAC CGC CGG GCC AAA TGG CGA CAC CAG AAG CGC GCG     1398
Val Trp Phe Lys Asn Arg Arg Ala Lys Trp Arg His Gln Lys Arg Ala
                175                 180                 185

TCG GCT TCC GCG AGG CTC CTG CCC GGC GTC AAG AAG TCC CCG AAG GGG     1446
Ser Ala Ser Ala Arg Leu Leu Pro Gly Val Lys Lys Ser Pro Lys Gly
                190                 195                 200

AGC TGC TGA TGA CTCTAGGAGC TGCCCCTGGG CTCGGCCACC CTTTTTGGGA         1498
Ser Cys  *   *
    205

TCTTTGGAGT TGGCGCTGAG AGAAGACAGG TCTACCCGAA AAGGAGCTGG GAGAGTACAC    1558

CGGCCGCCTC CACCCGTCTC CACAGCCCTT GCCTCCTGCA GCTCGTGCTG CCGTGGCGCT    1618

GGGGACGGGC CCCCGGTGCT TGGTGTTCCA CGGCAGTGGG AGTGGCGAGT CCCTTGGGGG    1678

TGGGCTGGGG CATAGAGCAG TTTCCTCAGC TCCCTACCCC CCGAGAGACA CTAACTCCAC    1738

CGCAGGAGGG GAACCACCCC GTATCAACAC GGGACCCAGA ATCCTACGCA GTGGAGCGTC    1798

TCTCCGCACC CTGGGACATG CTGGCCACCC TCTTCTCAAT GTGGACATTG ACCTAACTTG    1858

ACCTGGCTCG TCCTCCCCCA GCGGGAGAGG GGATGGGGTT CGTGTCTGTG CAGTCCTGGC    1918

GTTGCAGGCT TCCCAGGCCC TGGGCTGGGT CTTGGTATCT GGACCTGTAG AATAAGAAGG    1978

TCGCAGGAGC GATTCCAGGA GCCCCTCCAC AGTCCCTTCA CCTTCGAGCC TCGCGCTGAT    2038

ACTGAGAAAC TAGCAACTTC AAATACCACA GAAGCCGCCC AGAGTCTCAA GTCCACCTTG    2098

GCTCCACTCC CACACCCAAC AAGGAGCTGT CCCTTCTTCT TCCTTCCCAG CGAGGGGGTA    2158

TTTAGGGTAC AGCTGTCTTT GAGAGGAGCA CAGCTCAGCG ATCCTCAGTC TCTGCACCAG    2218

GGTGCTCCCC AGCAGAGGGG ACTGCTCCAC GGATGGTGGC CTTGGACCCC TGGGGTCCAG    2278

CCCTGGCCTC TAGGCTACTG TGAACCTGCC CATGGGTGAG GTCCCCTGC TTCCTCCTGG     2338

GGTTTTCATG CTGTGGGCTC GGACTCCCTC ACAGCAATCT GTGCCATCCT AGGGTAGGGC    2398

AAGAGGAGGT TGGACTGGGG AGACCCCGCC CTGCTGCCT GGGAAGATGC CTGCCCTCCC     2458

CTTCTTTATC CTGGCCCATG GCAAAAGGCA CAGTGGAAAG AAGCCTTAGA TTCCCCAAGT    2518

AGGCCCTACA GTGGGTCCAA AGCATCTCAC ATCCCCACCC CCAGCTGGCT TGAGCACCTC    2578

GTTCTGTCTC CTTACAGGCC TGCAGGGAA TGGGCCATT CTACCTGCAA GAGATGAAGT      2638

CCATCTCTAA AAGCAGGACT GCAGAAGCCA GGGCTGCAGC TCCCCAGACA CCCCAAGGCT    2698
```

```
GGCCAGCTTG GATAACACCA AGCAAGCATG GTGTCCCCAG TCAGAACTGC CCTGACACTG      2758

CTGGGTGTCC CTAGCATCCC CGCCTCCACC CCTAGCATGC ACACAAAGCC CTTCTCCCTG      2818

AACCCTGGTC TTGCCCTTGG GGACTGAACA GACTACCTGT GGACATGCCC GTGTCCCAGT      2878

CAGCTCCCTT GCAGCTGGGG ACACTCGCAT CTCACAGGCT CCAGGCCCCT TGAGTTCCTT      2938

GGTTGAATGG CCATCTGTCA TTGTTTTGGG AGCCCCGATC AGAGCTTGTG GAGCGCCACC      2998

TTCCAGGGCT CAGTGGCTGT GTTGCTCTCC TGAATTTGCT TCTTGAGCTC TAGCTGCTCC      3058

TTGGCAGGCT GACCCCCCAC AGCAGGCTAT TAACATAGGC ATCCTTCACG CTCACACCCA      3118

GGCGCTCGCT TCTCATCTTC ACCCTCTTCC CGGTTTATCT TTTACCCTCA GACTCCAATT      3178

CCCATCTTTC TGCCACATTT ACATCTCAAG CCAGGCACTT CCCCTGAGCC AGGTATTTAT      3238

CTCCAGCTGT CCCCTTGAAG CCCACAGACT CCTTAAGGTC ACCTTGTCCA CAGTGAGCTC      3298

TTCTGTGCAA ACCAGGCACA TGAGCCAGAG AGCTAGCCGC CCACCCGAAA CTGGTCCCTG      3358

GACCCCTCCC TCTCCTGATC ATCCACTATA CCCAGGCTGA CAGGAAGTCA GTTTTACTGT      3418

TTATCAATAA ATCAATAAAT CCCAGAATCT CTCCAGCTCT AACTGCACCA GTCTGATGTA      3478

AGCCACCGTC ACCTCTCACC TTGACCACT                                       3507
```

(2) INFORMATION FOR SEQ ID NO:37:

(i) SEQUENCE CHARACTERISTICS:
        (A) LENGTH: 205 amino acids
        (B) TYPE: amino acid
        (D) TOPOLOGY: linear (ii) MOLECULE TYPE: protein (xi) SEQUENCE DESCRIPTION: SEQ ID NO:37:

```
Met Ala Ala Ala Gly Gly Ala Ala Ser Arg Arg Gly Ala Gly Arg
 1               5                  10                  15

Pro Cys Pro Phe Ser Ile Glu His Ile Leu Ser Ser Leu Pro Glu Arg
                20                  25                  30

Ser Leu Pro Ala Arg Ala Ala Cys Pro Pro Gln Pro Ala Gly Arg Gln
            35                  40                  45

Ser Pro Ala Lys Pro Glu Glu Pro Gly Ala Pro Glu Ala Ala Pro Cys
 50                  55                  60

Ala Cys Cys Cys Cys Gly Pro Arg Ala Ala Pro Cys Gly Pro Pro
 65                  70                  75                  80

Glu Ala Ala Ala Gly Leu Gly Ala Arg Leu Ala Trp Pro Leu Arg Leu
                85                  90                  95

Gly Pro Ala Val Pro Leu Ser Leu Gly Ala Pro Ala Gly Gly Ser Gly
            100                 105                 110

Ala Leu Pro Gly Ala Val Gly Pro Gly Ser Gln Arg Arg Thr Arg Arg
            115                 120                 125

His Arg Thr Ile Phe Ser Glu Glu Gln Leu Gln Ala Leu Glu Ala Leu
            130                 135                 140

Phe Val Gln Asn Gln Tyr Pro Asp Val Ser Thr Arg Glu Arg Leu Ala
145                 150                 155                 160

Gly Arg Ile Arg Leu Arg Glu Glu Arg Val Glu Val Trp Phe Lys Asn
                165                 170                 175

Arg Arg Ala Lys Trp Arg His Gln Lys Arg Ala Ser Ala Ser Ala Arg
                180                 185                 190

Leu Leu Pro Gly Val Lys Lys Ser Pro Lys Gly Ser Cys
            195                 200                 205
```

(2) INFORMATION FOR SEQ ID NO:38:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:38:

```
Lys Arg Arg His Arg Thr Ile Phe Thr Asp Glu Gln Leu Glu Ala Leu
  1               5                  10                  15
Glu Asn Leu Phe Gln Glu Thr Lys Tyr Pro Asp Val Gly Thr Arg Glu
             20                  25                  30
Gln Leu Ala Arg Lys Val His Leu Arg Glu Glu Lys Val Glu Val Trp
         35                  40                  45
Phe Lys Asn Arg Arg Ala Lys Trp Arg Arg Gln Lys
     50                  55                  60
```

(2) INFORMATION FOR SEQ ID NO:39:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:39:

```
Thr Arg Arg His Arg Thr Ile Phe Ser Glu Glu Gln Leu Gln Ala Leu
  1               5                  10                  15
Glu Ala Leu Phe Val Gln Asn Gln Tyr Pro Asp Val Ser Thr Arg Glu
             20                  25                  30
Arg Leu Ala Gly Arg Ile Arg Leu Arg Glu Glu Arg Val Glu Val Trp
         35                  40                  45
Phe Lys Asn Arg Arg Ala Lys Trp Arg His Gln Lys
     50                  55                  60
```

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

ATGGCGGCAG CGGCTGGGGG CGC                                         23

(2) INFORMATION FOR SEQ ID NO:41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

-continued

```
       (xi) SEQUENCE DESCRIPTION: SEQ ID NO:41:

CTTCAGCGAA GAGCAGCTG                                                    19

(2) INFORMATION FOR SEQ ID NO:42:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:42:

TATCCTGACG TGAGTACGCG                                                   20

(2) INFORMATION FOR SEQ ID NO:43:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:43:

AAATGGCGAC ACCAGAAGC                                                    19

(2) INFORMATION FOR SEQ ID NO:44:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:44:

CCGGCGTCAA GAAGTCCCCG AAGGGG                                            26

(2) INFORMATION FOR SEQ ID NO:45:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:45:

TCCCTCTCCT GATCATCCAC                                                   20
```